US005772926A

United States Patent [19]
Akhavan-Tafti

[11] Patent Number: 5,772,926
[45] Date of Patent: Jun. 30, 1998

[54] CHEMILUMINESCENT REACTIONS USING DIHYDROXYAROMATIC COMPOUNDS AND HETEROCYCLIC ENOL PHOSPHATES

[75] Inventor: Hashem Akhavan-Tafti, Brighton, Mich.

[73] Assignee: Lumigen, Inc., Southfield, Mich.

[21] Appl. No.: 855,421

[22] Filed: May 13, 1997

[51] Int. Cl.[6] ............................. C09K 3/00; C12Q 1/00
[52] U.S. Cl. .................................. 252/700; 435/4
[58] Field of Search ................... 252/700; 435/4

[56] References Cited

U.S. PATENT DOCUMENTS

| | | | |
|---|---|---|---|
| 5,306,621 | 4/1994 | Kricka | 435/7.91 |
| 5,393,469 | 2/1995 | Akhavan-Tafti | 252/700 |
| 5,451,347 | 9/1995 | Akhavan-Tafti et al. | 252/700 |
| 5,578,498 | 11/1996 | Singh et al. | 252/700 |
| 5,589,328 | 12/1996 | Mahant | 435/4 |
| 5,595,875 | 1/1997 | Law et al. | 435/6 |

FOREIGN PATENT DOCUMENTS

| | | |
|---|---|---|
| 96/07911 | 3/1996 | WIPO . |
| 97/26245 | 7/1997 | WIPO . |

OTHER PUBLICATIONS

M. Maeda, A. Tsuji, K.H. Yang, S. Kamada, Biolum. and Chemilum. Current Status, 119–22 (91) (1991).
M. Kitamura, M. Maeda, A. Tsuji, J. Biolum. Chemilum., 10, 1–7 (1995).
H. Sasamoto, M. Maeda, A. Tsuji, Anal. Chim. Acta, 306, 161–6 (1995).
H. Arakawa, M. Maeda, A. Tsuji, Anal. Biochem. 199, 238–242 (1991).
A.P. Schaap, M.D. Sandison, and R.S. Handley, Tetrahedron Letters, 1159 (1987).
A.P. Schaap, T.S. Chen, R.S. Handley, R. DeSilva and B.P. Giri, Tetrahedron Lett., 1155 (1987).
A.P. Schaap, R.S. Handley, and B.P. Giri, Tetrahedron Lett., (1987).
A.P. Schaap, Photochem. Photobiol., 47S, 50S (1988).
N. Ugarova, et al., Biolum. and Chemilum. New Perspectives, Stanley etal eds., Wiley, 511–4 (1981).
W. Miska, R. Geiger, J. Biolum. Chemilum., 4, 119–28 (1989).
K. Sasamoto, Y. Ohkura, Chem. Pharm. Bull., 38, 1323–5 (1991).
M. Nakazono, H. Nohta, K. Sasamoto, Y. Ohkura, Anal. Sci., 8, 779–83 (1992).
A. Tsuji, M. Maeda, H. Arakawa, Anal. Sci., 5, 497–506 (1989).
J. Alam, J. Cook, Anal. Biochem. 188, 245–54 (1990).
R. B. McComb et al. Alkaline Phosphatases, Plenum Press, NY 1979, 268–75, 332–4, 394–7, 410–3.

Primary Examiner—Philip Tucker
Attorney, Agent, or Firm—Richard S. Handley

[57] ABSTRACT

Novel methods and compositions which generate chemiluminescence are provided. The compositions comprise a heterocyclic enol phosphate compound and a dihydroxyaromatic compound in which the two hydroxy groups are separated by an even number of ring carbon atoms.

Novel methods and compositions for generating chemiluminescence by reaction with a hydrolytic enzyme are provided as well. The compositions comprise a heterocyclic enol phosphate compound and a protected dihydroxyaromatic compound in which one of the hydroxy groups of the dihydroxyaromatic compound is protected with an enzyme-cleavable group.

The novel chemiluminescent compositions are useful in methods for producing chemiluminescence for use in assays of hydrolytic enzymes and enzyme inhibitors and in assays employing labeled specific binding pairs.

72 Claims, 8 Drawing Sheets

CHEMILUMINESCENT REACTIONS USING DIHYDROXYAROMATIC COMPOUNDS AND HETEROCYCLIC ENOL PHOSPHATES

FIELD OF THE INVENTION

The present invention relates to chemiluminescent methods and compositions for generating chemiluminescence. In particular, the present invention relates to methods of generating chemiluminescence comprising reacting a dihydroxyaromatic compound and a heterocyclic enol phosphate compound in the presence of oxygen. The present invention also relates to chemiluminescent methods and compositions for generating chemiluminescence by the action of a hydrolytic enzyme. The methods for generating chemiluminescence comprise reacting a hydrolytic enzyme with a protected dihydroxy-aromatic compound in which one of the hydroxy groups is protected with an enzyme cleavable group to release the dihydroxyaromatic compound for reaction with a heterocyclic enol phosphate compound to produce chemiluminescence. The invention further relates to the use of the present chemiluminescent methods in assays for detecting analytes including hydrolytic enzymes and enzyme-labeled specific binding partners in specific binding pair assays including immunoassays, nucleic acid probe assays and the like.

BACKGROUND OF THE INVENTION

1. Chemiluminescent Detection of Hydrolytic Enzymes

Hydrolytic enzymes such as alkaline phosphatase and β-galactosidase are frequently used as markers or labels in enzyme-linked assays for biological molecules and other analytes of interest such as drugs, hormones, steroids and cancer markers. In addition, phosphatase enzymes, e.g. alkaline phosphatase (AP) and acid phosphatase (AcP), are clinically significant in their own right in human and veterinary diagnostics. Chemiluminescent detection of these enzymes offers a safe, convenient and sensitive means to provide a quantitative measure of the amount of enzyme in a sample or of the amount of an enzyme-labeled analyte or labeled specific binding partner for an analyte. Numerous chemiluminescent reaction schemes are known in the art for quantitating the level of particular hydrolytic enzymes. Many of these schemes are complex and expensive, requiring multiple enzymes or several reagents. Commercial acceptance of such methods for large volume testing has been slow.

a. Chemiluminescent Reaction of Acridan Compounds with Alkaline Phosphatase. PCT Application US97/00015, filed on Jan. 15, 1997 describes a chemiluminescent reaction between a phosphatase enzyme and a compound comprising an heterocyclic ring group and an enol phosphate group. Also described is the improvement afforded by incorporation of a cationic aromatic compound in the chemiluminescent reaction between a phosphatase and the heterocyclic enol phosphate compound. In contrast to the present methods, the methods disclosed in these applications rely on the reaction of a phosphatase enzyme with this heterocyclic enol phosphate compound to cleave the phosphate group. In the present methods, no enzyme is used to cleave the phosphate group.

b. Reactions Involving the Generation of Reducing Agents. Chemiluminescent methods involving the generation of a reducing agent from a phosphate ester catalyzed by alkaline phosphatase have been reported. (M. Maeda, A. Tsuji, K. H. Yang, S. Kamada, Biolum. and Chemilum. Current Status, 119–22 (1991); M. Kitamura, M. Maeda, A. Tsuji, J. Biolumin. Chemilumin., 10, 1–7 (1995); H. Sasamoto, M. Maeda, A. Tsuji, Anal. Chim. Acta, 306, 161–6 (1995)). The reducing agent reacts with oxygen and lucigenin to produce light. Representative reducing agents include ascorbic acid, glycerol, NADH, dihydroxyacetone, cortisol and phenacyl alcohol. A PCT application, WO96/04400, and a publication (H. Arakawa, M. Maeda, A. Tsuji, Anal. Biochem., 199, 238–242 (1991)) also describe chemiluminescent assays of alkaline phosphatase using indoxyl phosphate compounds and other related phosphate compounds which produce reducing species on dephosphorylation. Chemiluminescence is produced in the presence of lucigenin or other luminescence amplifying agents by virtue of their reaction with $H_2O_2$ or superoxide ion.

U.S. Pat. No. 5,589,328 to Mahant discloses a chemiluminescent reaction whereby indoxyl esters, thioindoxyl esters and benzofuran esters are hydrolyzed by an enzyme and thereby generate superoxide. Luminescence is amplified by adding a chemiluminescence generating reagent such as lucigenin. Lucigenin produces chemiluminescence by reaction with superoxide.

c. Enzymatically Triggerable Dioxetanes. Stable 1,2-dioxetanes bearing a protected phenol triggering group undergo a chemiluminescent decomposition upon removal of a protecting group (A. P. Schaap, T. S. Chen, R. S. Handley, R. DeSilva, and B. P. Giri, Tetrahedron Lett., 1155 (1987); A. P. Schaap, R. S. Handley, and B. P. Giri, Tetrahedron Lett., 935 (1987); A. P. Schaap, M. D. Sandison, and R. S. Handley, Tetrahedron Lett., 1159 (1987); and A. P. Schaap, Photochem. Photobiol., 47S, 50S (1988)). Such enzymatically triggerable dioxetanes are triggered by reaction with a hydrolytic enzyme to thereby accelerate the chemiluminescent decomposition rate of the dioxetane by orders of magnitude. Numerous examples of such triggerable dioxetanes are now known in the art. However, an inherent disadvantage of most triggerable dioxetanes is their tendency to generate background chemiluminescence in the absence of enzyme through slow thermal decomposition or non-enzymatic hydrolysis.

d. Luciferin Derivatives. Phosphate and galactoside derivatives of firefly luciferin are known (N. Ugarova, Y. Vosny, G. Kutuzova, I. Dementieva, Biolum. and Chemilum. New Perspectives, P. Stanley and L. J. Kricka, eds., Wiley, Chichester, 511–4 (1981); W. Miska, R. Geiger, J. Biolumin. Chemilumin., 4, 119–28 (1989)). Treatment of the firefly luciferin derivative with the appropriate enzyme liberates firefly luciferin which is reacted in a second step with luciferase and ATP to produce light.

e. Luminol Derivatives. A phosphate and a NAG derivative of luminol are known (K. Sasamoto, Y. Ohkura, Chem. Pharm. Bull., 38, 1323–5 (1991); M. Nakazono, H. Nohta, K. Sasamoto, Y. Ohkura, Anal. Sci., 8, 779–83 (1992)). Treatment of the luminol derivative with the appropriate enzyme liberates luminol which is reacted in a subsequent step with ferricyanide to produce light.

f. Coupled Enzyme Methods. Applicants' PCT application WO 96/07911 discloses the enzymatic generation of a phenolic enhancer from a protected phenol compound using a hydrolytic enzyme. The phenol compound enhances the chemiluminescent oxidation of acridancarboxylic acid derivatives with a peroxidase enzyme. U.S. Pat No. 5,306,621 discloses a similar coupled enzyme reaction where a dihydrophthalazinedione is used as the chemiluminescent peroxidase substrate. Protected dihydroxyaromatic compounds in which one of the hydroxy groups is protected with a group cleavable by a hydrolytic enzyme are not usable in these methods since dihydroxyaromatic compounds are not peroxidase enhancers. Numerous other chemiluminescent methods and assays for determining hydrolytic enzymes such as phosphatase enzymes through coupled enzyme reactions are known. A compilation of such methods is listed in A. Tsuji, M. Maeda, H. Arakawa, Anal. Sci., 5, 497–506 (1989). All of the coupled enzyme methods require two or more enzymes and utilize either luminol or a luminol analog, lucigenin or bacterial luciferin as the chemiluminescent species.

Many of the aforementioned methods suffer the drawback of requiring multiple reagents or enzymes in order to generate the luminescent signal. The added expense or operational complexity has hindered commercial acceptance of these methods in spite of their demonstrated exceptional detection sensitivity. Chemiluminescent methods for detecting and quantitating hydrolytic enzymes which achieve these levels of sensitivity but do not require additional enzymes or auxiliary reagents in addition to the enzyme substrate would be advantageous. The present invention provides such methods and compounds.

2. Enzymatic Release of Electron-Transfer Agents (ETA)

a. Colorimetric and Fluorimetric Detection U.S. Pat. No. 4,952,495 discloses and claims methods for determination of hydrolytic enzymes by the enzymatic formation of a substance capable of mediating an electron-transfer reaction leading to the production of a detectable species. The ETA can comprise in one embodiment a reducing substance such as a substituted hydroquinone compound. The detectable species form a colored or fluorescent product. It is further taught that the detectable species can be a shiftable detectable species comprising a quinone linked through a linking group to a chromogenic, fluorogenic or chemiluminogenic species. There is no teaching or suggestion of any chemiluminogenic detectable species other than such a shiftable compound. There is no suggestion or teaching of the presently described heterocyclic enol phosphate compounds.

b. Amperometric Detection of Alkaline Phosphatase (AP) A method is known for the amperometric detection of alkaline phosphatase comprising the enzymatic generation of hydroquinone from its monophosphate by AP, oxidation of the hydroquinone at the surface of an electrode to produce benzoquinone, regeneration of hydroquinone by the second enzyme glucose oxidase which transfers electrons from it substrate glucose. The quantity of AP is detected as an increase in electrical current.

SUMMARY OF THE INVENTION

It is an object of the present invention to provide a method of generating chemiluminescence by reacting a dihydroxyaromatic compound with a second compound containing a heterocyclic ring group and an enol phosphate group which undergoes a reaction in the presence of oxygen to produce chemiluminescence.

It is another object of the present invention to provide a method of generating chemiluminescence by the action of a hydrolytic enzyme comprising a) reacting the hydrolytic enzyme with a protected dihydroxyaromatic compound in which one of the hydroxy groups is protected with a group cleavable by the hydrolytic enzyme to produce a dihydroxyaromatic compound; and b) reacting the dihydroxyaromatic compound with a heterocyclic enol phosphate compound to produce chemiluminescence.

It is a further object of the present invention to provide chemiluminescent compositions comprising a dihydroxyaromatic compound and a heterocyclic enol phosphate compound. It is still a further object of the present invention to provide compositions which produce chemiluminescence upon reaction with a hydrolytic enzyme wherein the composition comprises a protected dihydroxyaromatic compound in which one of the hydroxy groups is protected with a group cleavable by the hydrolytic enzyme and a heterocyclic enol phosphate compound.

Another object of the present invention to provide methods for conducting an assay of an analyte comprising reacting a dihydroxyaromatic compound with a heterocyclic enol phosphate compound to produce chemiluminescence, measuring the chemiluminescence and relating the chemiluminescence to the amount of the analyte.

A further object is to provide a method of conducting an assay of an analyte comprising reacting a dihydroxyaromatic compound and a heterocyclic enol phosphate compound to produce chemiluminescence, measuring the chemiluminescence and relating the chemiluminescence to the amount of the analyte, wherein the heterocyclic enol phosphate compound is provided as a label on a specific binding pair member.

A further object is to provide a method of conducting an assay of an analyte comprising reacting a hydrolytic enzyme, a protected dihydroxyaromatic compound and a heterocyclic enol phosphate compound to produce chemiluminescence, measuring the chemiluminescence and relating the chemiluminescence to the amount of the analyte.

It is yet another object of the present invention to provide a method of detecting a hydrolytic enzyme in a sample which comprises reacting the sample containing or suspected of containing the hydrolytic enzyme with a protected dihydroxyaromatic compound in which one of the hydroxy groups is protected with an enzyme-cleavable group in the presence of a heterocyclic enol phosphate compound to produce chemiluminescence and relating the chemiluminescence to the amount of the hydrolytic enzyme in the sample.

A further object is to provide a method of conducting an assay of an analyte comprising reacting a hydrolytic enzyme, a protected dihydroxyaromatic compound and a heterocyclic enol phosphate compound to produce chemiluminescence, measuring the chemiluminescence and relating the chemiluminescence to the amount of the analyte, wherein the hydrolytic enzyme is provided as a label on a specific binding pair member.

DESCRIPTION OF THE PREFERRED EMBODIMENTS

Definitions

Figure 1:
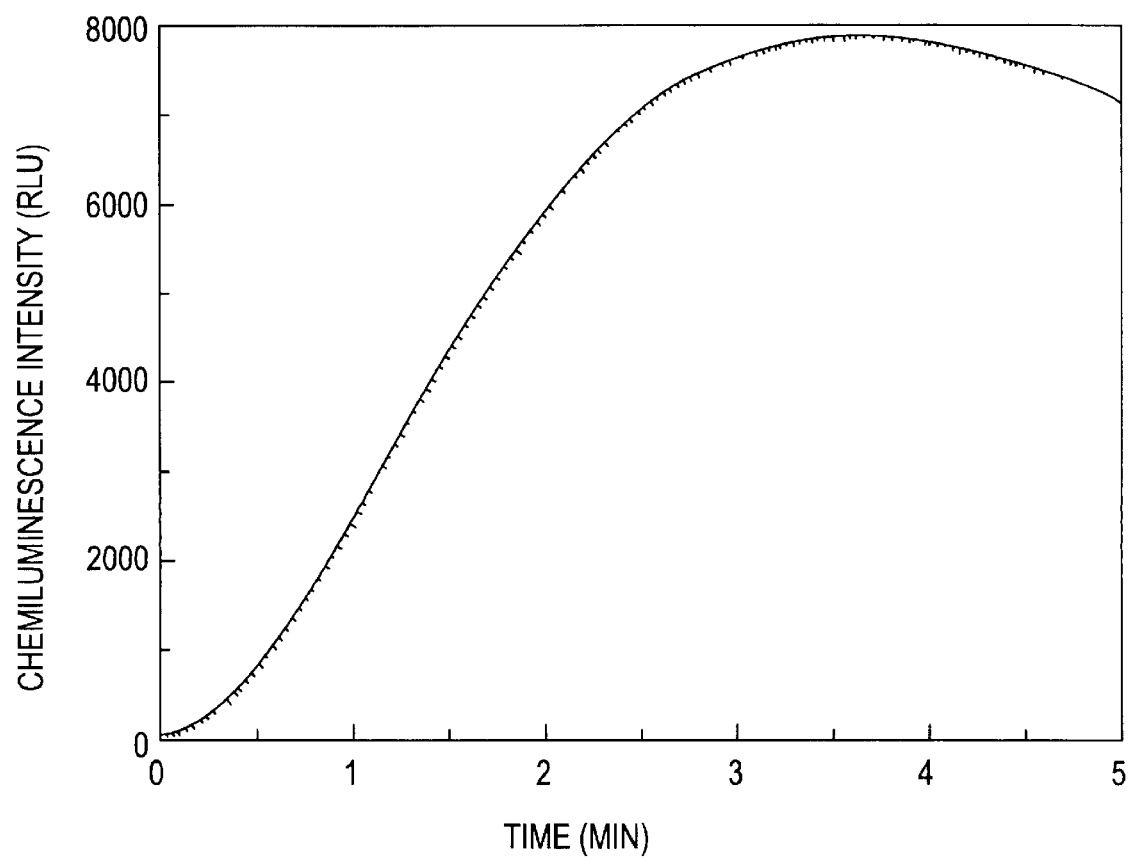
FIG. 1 is a plot showing the rapid generation of chemiluminescence from the reaction of acridan phosphate 1 with hydroquinone at room temperature. The reaction mixture comprised 0.66 mM acridan phosphate 1 and 4 $\mu$M hydroquinone in 2-methyl-2-amino-1-propanol (221) buffer, 0.2M, pH 9.6 also containing 0.88 mM $MgCl_2$.

Alkyl—A branched, straight chain or cyclic hydrocarbon group containing from 1–20 carbons. Lower alkyl as used herein refers to those alkyl groups containing up to 8 carbons.

Alkenyl—A branched, straight chain or cyclic hydrocarbon group containing at least one C—C double bond and containing from 2–20 carbons. Lower alkenyl as used herein refers to those alkenyl groups containing up to 8 carbons.

Alkynyl—A branched or straight chain hydrocarbon group containing at least one C—C triple bond and containing from 2–20 carbons. Lower alkynyl as used herein refers to those alkynyl groups containing up to 8 carbons.

Analyte—A substance the presence or amount of which is to be measured in a sample by an assay. Analytes include organic and biological molecules to which a specific binding partner having a specific binding affinity exists. Exemplary analytes include, without limitation, single stranded or double stranded DNA, RNA, DNA-RNA complexes, oligonucleotides, antibodies, antibody fragments, antibody-DNA chimeras, antigens, haptens, proteins, lectins, avidin, streptavidin and biotin. Other exemplary analytes also include hydrolytic enzymes, inhibitors of hydrolytic enzymes and dihydroxyaromatic compounds.

Aryl—An aromatic ring-containing group containing 1 to 5 carbocyclic aromatic rings, which can be substituted with 1 or more substituents other than H.

Biomedical analysis—Analyses of samples of biological origin for analytes of interest. The analyses can be immunoassays, western blots, northern blots, Southern blots, DNA hybridization assays, DNA sequence analysis, colony hybridizations, gene expression analysis, high throughput drug screening, detection of infectious agents or pathogens and the like.

Dihydroxyaromatic compound—An aromatic ring compound comprising an aromatic ring system, in turn comprising at least one carbocyclic ring and up to five rings, which is substituted with two hydroxy groups which are separated by an even number of ring carbon atoms. This substitution pattern is exemplified by the ortho- and para- substitution pattern on a benzene ring and by e.g. 1,2-, 1,4- or 2,6- substitution pattern on a naphthalene ring. Dihydroxy-substituted biaryl ring systems such as biphenyl and binaphthyl are considered to be within the scope of the definition subject to the limitation of there being an even number of ring carbon atoms separating the two hydroxy groups. A dihydroxyaromatic compound can be substituted with additional hydroxy groups, i.e. trihydroxy, tetrahydroxy etc. and still be within the scope of the definition provided that at least one pair of hydroxy groups is separated by an even number of ring carbon atoms.

Halogen—Fluorine, chlorine, bromine or iodine atoms.

Sample—A fluid containing or suspected of containing one or more analytes to be assayed. Typical samples which are analyzed by the chemiluminescent reaction method are biological samples including body fluids such as blood, plasma, serum, urine, semen, saliva, cell lysates, tissue extracts and the like. Other types of samples include food samples and environmental samples such as soil or water.

Specific binding pair—Two substance which exhibit a mutual binding affinity. Examples include antigen-antibody, hapten-antibody or antibody-antibody pairs, complementary oligonucleotides or polynucleotides, avidin-biotin, streptavidin-biotin, hormone-receptor, lectin-carbohydrate, IgG-protein A, nucleic acid-nucleic acid binding protein and nucleic acid-anti-nucleic acid antibody.

It should be noted that in references to "a heterocyclic enol phosphate compound" or "a dihydroxyaromatic compound" or "a protected dihydroxyaromatic compound", it is intended to include more than one of the described species unless clearly indicated to be only the singular case.

It has been unexpectedly discovered that certain dihydroxyaromatic compounds comprising an aromatic ring system substituted with at least two hydroxy groups separated by an even number of ring carbon atoms react with a second compound which is a heterocyclic enol phosphate compound containing a heterocyclic ring group and an enol phosphate group in the presence of oxygen to generate easily detectable chemiluminescence. Exemplary aromatic ring systems embodied within the dihydroxyaromatic compounds of the present invention include benzene, biphenyl, naphthalene, anthracene, phenanthrene, pyrene, benzpyrene and naphthacene ring systems.

A preferred group of dihydroxyaromatic compounds have the formula I

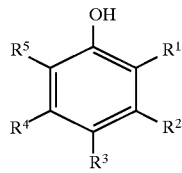

wherein at least one of $R^1$ and $R^3$ is an OH group, the other one of $R^1$ or $R^3$ and $R^2$, $R^4$ and $R^5$ are each independently selected from hydrogen, alkyl, alkoxy, alkenyl, alkynyl, aryl, aralkyl, amino, aminoalkyl, carboxyl —C(=O)OH, carboxyl ester —C(=O)OR$^6$, formyl —C(=O)H, alkylcarboxy —OC(=O)R$^6$, arylcarboxy —OC(=O)R$^9$ and halogen groups wherein pairs of adjacent groups, when taken together, can complete a five or six-membered aliphatic or aromatic ring and wherein $R^6$ is a lower alkyl group, wherein $R^7$ and $R^8$ are each H or a lower alkyl group and wherein $R^9$ is an aryl ring group.

More preferred compounds of formula I are those compounds wherein $R^3$ is the OH group and $R^1$, $R^2$, $R^4$ and $R^5$ are independently selected from hydrogen, alkyl, alkoxy, halogen, aryl and aralkyl groups. Still more preferably, each of $R^2$, $R^4$ and $R^5$ are hydrogen and $R^1$ is selected from hydrogen, alkyl, alkoxy, halogen, aryl and aralkyl groups.

It is recognized that other dihydroxyaromatic compounds in addition to those with the two hydroxy groups substituted on the same six-membered ring are within the scope of the dihydroxyaromatic compounds and are effective in the present methods. Dihydroxyaromatic compounds containing a biaromatic ring system wherein the hydroxy groups reside on different six-membered rings are exemplary. Some particular examples of dihydroxyaromatic compounds which are useful in the methods of the present invention are listed in Table 1 for purposes of illustrating and not defining the scope of the invention.

TABLE 1

| | Dihydroxyaromatic compounds |
|---|---|
| DHA-1 | 2-Chlorohydroquinone |
| DHA-2 | Hydroquinone |
| DHA-3 | 2-Phenylhydroquinone |
| DHA-4 | 3,3,3',3'-Tetramethyl-1,1'-spirobisindane-5,5',6,6'-tetrol |
| DHA-5 | 2,3,5,6-Tetrafluorohydroquinone |
| DHA-6 | 2-Methylhydroquinone |
| DHA-7 | 2-Methoxyhydroquinone |
| DHA-8 | Catechol |
| DHA-9 | 1,2-Dihydroxyanthracene |
| DHA-10 | 7,8-Dihydroxy-6-methoxycoumarin |
| DHA-11 | 1-Methyl-6,7-dihydroxy-1,2,3,4-tetrahydroisoquinoline |
| DHA-12 | 4-Aminoresorcinol |
| DHA-13 | 1,4-Dihydroxynaphthalene |
| DHA-14 | 1,2,4-Trihydroxybenzene |
| DHA-15 | 9,10-Bis(4-hydroxyphenyl)anthracene |
| DHA-16 | 4-Bromoresorcinol |
| DHA-17 | 2,3-Dihydro-9,10-dihydroxy-1,4-anthraquinone |
| DHA-18 | Ellagic acid |
| DHA-19 | 2,5-Dihydroxybenzaldehyde |
| DHA-20 | 2,3-Dichloro-5,8-dihydroxy-1,4-naphthoquinone |

TABLE 1-continued

Dihydroxyaromatic compounds

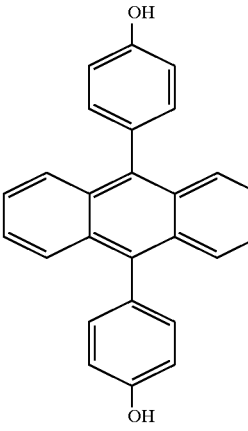

DHA-15     DHA-16

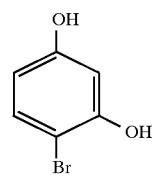

DHA-17

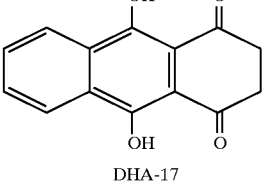

DHA-18

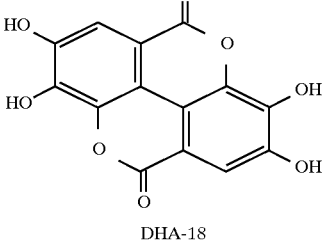

DHA-19     DHA-20

Heterocyclic enol phosphate compounds useful in the present methods and compositions for producing chemiluminescence have the formula:

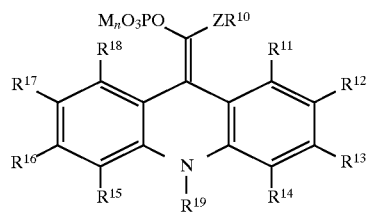

wherein $R^{10}$ is an organic group which allows the light to be produced, wherein each of $R^{11}$–$R^{18}$ are independently selected from and wherein pairs of adjacent groups can complete a benzo-fused ring, wherein $R^{19}$ is an organic group containing up to 50 atoms selected from C, N, O, S, P and halogen atoms, wherein Z is selected from O and S atoms, wherein each M is independently selected from H and a cationic center and wherein n is a number which satisfies electroneutrality. In compounds of formula III where double bond isomers are possible, mixtures of the two double bond isomers can be used.

Referring back to formula III, exemplary ring structures include the structures below where the asterisk denotes the position of the exocyclic double bond. Without explicitly showing all possible substitution patterns, it is to be understood that each ring position can contain substituents other than hydrogen.

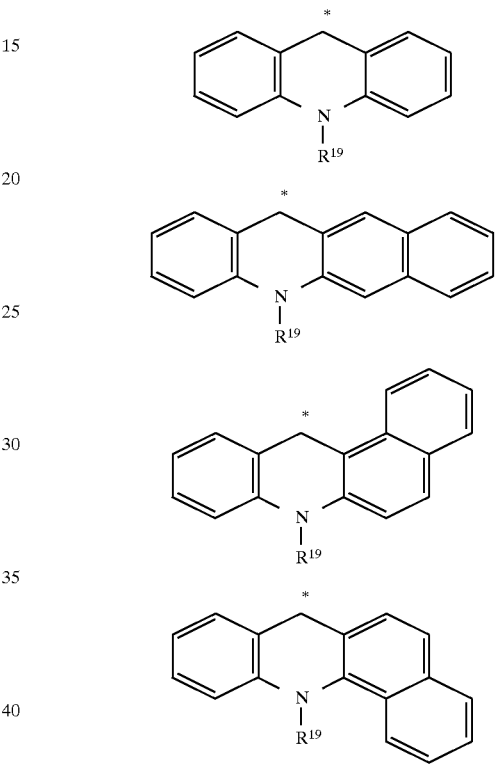

The group $R^{19}$ is preferably selected from alkyl, substituted alkyl, aryl, substituted aryl, aralkyl and substituted aralkyl groups. More preferred groups for $R^{19}$ include substituted and unsubstituted lower alkyl groups and substituted and unsubstituted benzyl groups.

In all of the above compounds, the groups $R^{11}$–$R^{18}$ each are independently H or a substituent group which permits the light to be produced and generally contain from 1 to 50 atoms selected from C, N, O, S, P and halogen atoms. Representative substituent groups which can be present include, without limitation, alkyl, substituted alkyl, aryl, substituted aryl, aralkyl, alkenyl, alkynyl, alkoxy, aryloxy, halogen, amino, substituted amino, carboxyl, carboalkoxy, carboxamide, cyano, and sulfonate groups. Pairs of adjacent groups, e.g. $R^{11}$–$R^{12}$, can be joined together to form a benzo-fused ring. Specific substituents and their effects are illustrated in the specific examples below, which, however, are not to be considered limiting the scope of the invention in any way.

Each of the groups M independently are a hydrogen atom or a cationic center. A cationic center means a positively charged atom such as a sodium ion Na⁺, a group of atoms such as an ammonium ion $NH_4^+$ or a portion of a molecule with one or more sites of positive charge. Examples of the latter include dicationic compounds described in U.S. Pat. No. 5,451,347 to applicant and polymeric compounds with multiple cationic groups as described in applicant's U.S. Pat. No. 5,393,469. The positive charge on a cationic center may take any unit value, i.e. 1, 2, 3 etc. Exemplary cationic centers include, without limitation, alkali metal ions, alkaline earth ions, quaternary ammonium ions and quaternary phosphonium ions and are present in the number required by their valence. If two groups are required to be present in the compound of formula I for electroneutrality, they may be the same or different. Preferred counter ions are the alkali metal ions. More preferred are sodium and potassium ions.

The organic group $R^{10}$ can be any group which allows light production. This means that the presence of any group as the $R^{10}$ group does not prevent the ability of the compound of formula III to ultimately produce chemiluminescence. By the latter is meant that when a compound of formula III is reacted with the dihydroxyaromatic compound in the presence of oxygen, chemiluminescence is produced immediately and may involve the production of one or more chemiluminescent intermediates.

The group $R^{10}$ preferably contains from 1 to 50 atoms selected from C, N, O, S, P and halogen atoms exclusive of the necessary number of H atoms required satisfy the valencies of the atoms in the group. Groups which can function as the $R^{10}$ group include, without limitation, alkyl, substituted alkyl, aryl, substituted aryl, aralkyl and substituted aralkyl groups. Substituent groups other than H atoms, such as ionic groups or polar groups, can be incorporated in various numbers and at selected positions on the carbon chain or ring of $R^{10}$ in order to modify the properties of the compound or to provide for convenience of synthesis of the final phosphate compound. Such properties include, for example, chemiluminescence quantum yield, rate of reaction with the enzyme, maximum intensity of light emission, duration of light emission, wavelength of light emission and solubility in the reaction medium. Specific substituents and their effects are illustrated in the specific examples below, which, however, are not to be considered limiting the scope of the invention in any way.

A preferred class of compounds has the formula IIIa below wherein Z is an O or S atom, wherein $R^{19}$ is a lower alkyl group and wherein Ar is an aryl ring group containing at least one carbocyclic aromatic ring and which can be further substituted.

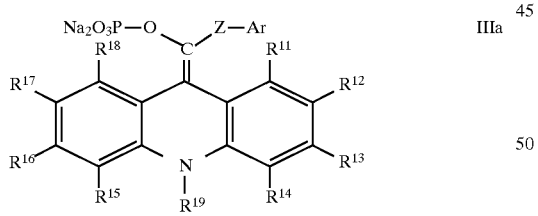

IIIa

The groups $R^{11}$ to $R^{18}$, which may be the same or different, each are a substituent which may contain from 1 to 50 atoms selected from C, H, N, O, S, P and halogen atoms and which permit the light to be produced and may include, without limitation, alkyl, substituted alkyl, aryl, substituted aryl, aralkyl such as benzyl, alkenyl, alkynyl, alkoxy, aryloxy, halogen, amino, substituted amino groups, carboxyl, carboalkoxy, carboxamide, cyano, and sulfonate groups. One preferred set of compounds has the groups $R^{11}$ to $R^{18}$ selected from hydrogen and lower alkoxy groups such as methoxy, ethoxy, t-butoxy and the like. Other preferred compounds have the formula IIIb where Z is O or S and Ar is selected from a phenyl group, a substituted phenyl group or a naphthyl group.

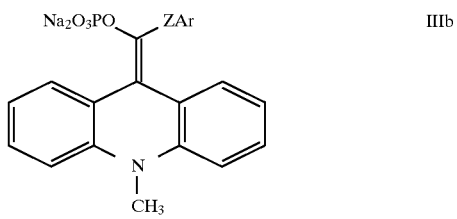

IIIb

Another preferred set of heterocyclic enol phosphate compounds contain a group —A—Q which permits the compound to be used as a label. Preferred labeling compounds contain the group —A—Q as a substituent on $R^{10}$ or $R^{19}$ or at any one of the $R^{11}$–$R^{18}$ positions. Examples of heterocyclic enol phosphate labeling compounds have formulas IIIc, d or e.

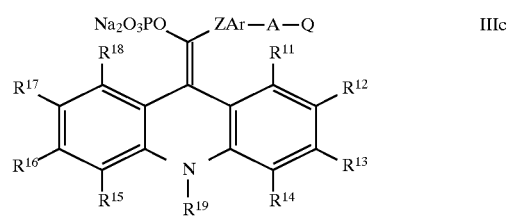

IIIc

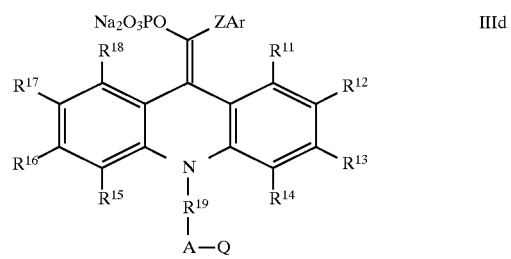

IIId

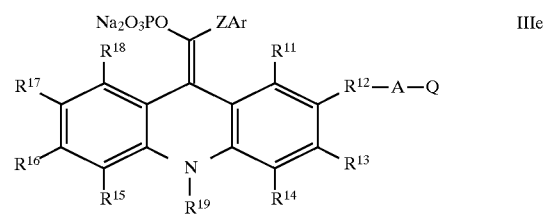

IIIe

In the group —A—Q, A is a spacer group selected from $C_1$–$C_{10}$ alkylene, and $C_2$–$C_{10}$ oxyalkylene groups and Q is a linking group capable of forming a covalent bond with a molecule to be conjugated such as an analyte or a specific binding partner. Linker groups Q can be electrophilic moieties such as halogen, diazo, —NCO, —NCS, —CHO, acid anhydride, oxiranyl, succinimidoxycarbonyl, maleimide, cyano, triazole and tetrazole groups and the like as are generally known in the art. Alternatively, linker groups Q can be nucleophilic moieties such as hydroxyl, —COOH, thiol, primary amino, secondary amino groups. In a compound of formula IIIe it is intended that the group A—Q can be present on either one of the two benzene rings.

The following specific compounds are particularly preferred for use in the presently described novel chemiluminescent methods:

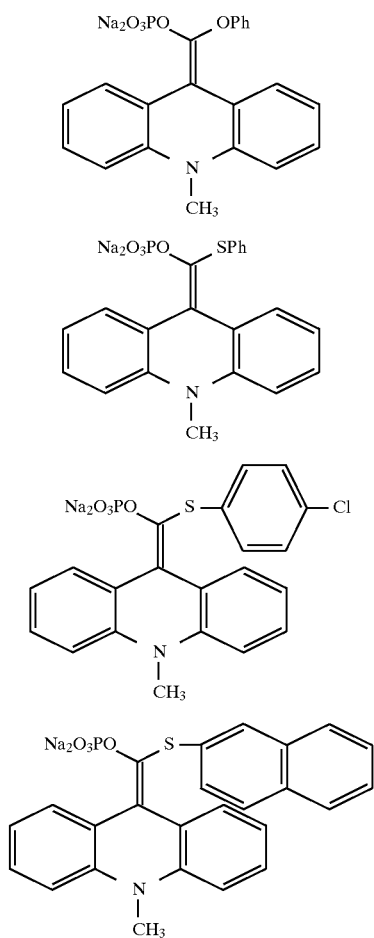

Reaction of a compound of formula III with a dihydroxyaromatic compound in an aqueous buffer solution produces bright chemiluminescence which rapidly reaches maximum intensity at room temperature.

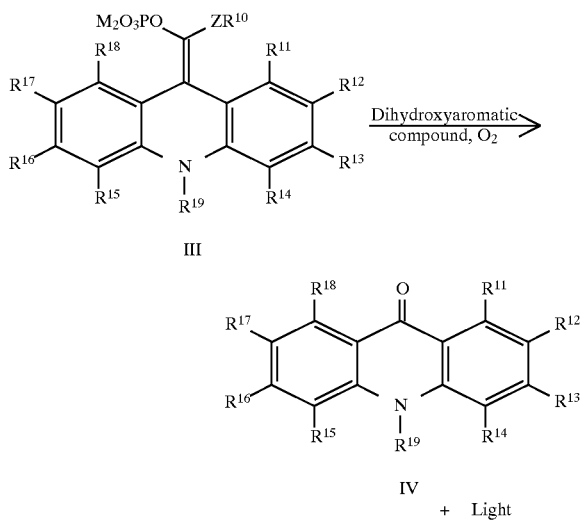

While we do not wish to put forth a specific mechanistic explanation for this discovery at this point, it is believed that chemiluminescence is emitted from the electronically excited state of a ketone compound IV formally derived from oxidation of the double bond of the heterocyclic enol phosphate compound. A necessary condition for the production of chemiluminescence is that the reaction produces sufficient energy to form the excited state of IV and that IV is fluorescent. The active oxidant may be oxygen, a reduced form of oxygen such as superoxide ion, peroxide ion or a peroxy radical, or the active oxidant may be an oxidized product of the dihydroxyaromatic compound, such as the quinone or semiquinone form.

Chemiluminescence emission from the present reactions and methods is typically produced as a 100–200 nm wide band of emission and exhibits a maximum intensity at wavelengths in the near ultraviolet to the visible region of the electromagnetic spectrum. Typical wavelengths of maximum intensity, $\lambda_{max}$, are in the range of 350–500 nm. It is contemplated that phosphate compounds of formula III bearing a covalently linked fluorophore could undergo intramolecular energy transfer resulting in emission at longer wavelengths from the excited state of the fluorophore.

Chemiluminescent light emitted by the present method can be detected visually or by any other suitable known means such as with a luminometer, x-ray film, high speed photographic film, a CCD camera, a scintillation counter or a chemical actinometer. Each detection means has a different spectral sensitivity. The human eye is optimally sensitive to green light, CCD cameras display maximum sensitivity to red light, x-ray films with maximum response to either UV, blue light or green light are available. Choice of the detection device will be governed by the application and considerations of cost, convenience, and whether creation of a permanent record is required.

The chemiluminescent reactions of the present invention comprising the reaction of compounds of formula I and III in the presence of oxygen may find use as chemical light sources, an example of which is the familiar light stick and related novelty items or for emergency lighting. Another use is in methods of detecting a compound of formula I in a sample in biomedical analysis, food analysis or environmental analysis of pollutants.

The chemiluminescent reactions of the present invention can also be used in a method of conducting an assay of an analyte in a sample by means of detectably labeled specific binding pairs. In one embodiment of such an assay method, either compound I or compound III is provided as a label compound. The label compound contains a substituent which bears a reactive labeling group, whereby the reactive group is capable of forming a covalent attachment to one member of a specific binding pair to form a detectably labeled specific binding pair member. The assay method further comprises reacting the labeled specific binding pair member and its partner for detecting the analyte to form a labeled specific binding pair and reacting the labeled specific binding pair with either compound I or compound III, as required, to produce chemiluminescence for detecting the analyte. Preferably the heterocyclic enol phosphate is provided as the label.

In another embodiment of an assay method, either compound I or compound III is provided as a detectable species encapsulated in a liposome which is conjugated to a specific binding pair member. Methods for preparing liposomes containing detectable species and their use as detectable labels in chemiluminescent assays are described in U.S. Pat. No. 5,595,875, which is incorporated herein by reference.

In another embodiment of an assay method, both compound I and compound III are each provided encapsulated in a separate latex particulate material to which are affixed complementary specific binding pair members. Methods for preparing latex particulate materials containing detectable species and their use as detectable labels in chemiluminescent assays are described in U.S. Pat. No. 5,578,498, which is incorporated herein by reference.

When measuring chemiluminescence in an assay procedure, the measurement can comprise measuring the light intensity at a fixed point in time relative to the event in the assay procedure, or at a series of time points or measuring the maximum instantaneous intensity or measuring the total quantity of light or the period of time until a specified light intensity is reached.

In practicing the methods of the present invention, oxygen is typically supplied dissolved in a solution of the reactants at equilibrium with the atmosphere. The atmosphere above the solution can be enriched or replaced with oxygen in order to increase the concentration of dissolved oxygen. The solution can also be placed in a sealed vessel capable of being pressurized and the gas space in the vessel pressurized with oxygen. Other modes of delivering oxygen, for example, sparging air or oxygen or generating oxygen by a chemical reaction are considered to fall within the scope of the methods described and claimed herein.

In another aspect, the present invention relates to reagent compositions for producing chemiluminescence comprising an aqueous buffer with a pH in the range of 7–10.5, a compound of formula I at a concentration of 0.001–20 mM and a compound of formula III at a concentration of 0.001–20 mM. Preferably the pH is in the range of 8–10 and more preferably the pH is in the range of 9–10.

In a preferred embodiment the composition additionally comprises an anionic surfactant at a concentration preferably between 0.001 and 5 mg/mL in the final reaction solution, more preferably between 0.01 and 2.5 mg/mL.

A preferred reagent composition for producing chemiluminescence comprises an aqueous buffer with a pH in the range of 8–10, a dihydroxyaromatic compound of formula I at a concentration of about 0.05–5 mM, an acridan phosphate of formula IIIc at a concentration of about 0.05–5 mM and optionally, an anionic surfactant at a concentration preferably between 0.01 and 2.5 mg/mL. In a more preferred composition, the dihydroxyaromatic compound of formula I is selected from hydroquinone, 2-chlorohydroquinone, 2-phenylhydroquinone and 2,3,5,6-tetrafluorohydroquinone.

Chemiluminescent Detection of Hydrolytic Enzymes

The present chemiluminescent reaction can serve as the basis for an enzymatic chemiluminescent reaction wherein a dihydroxyaromatic compound is produced by the reaction of a hydrolytic enzyme with a protected dihydroxyaromatic compound in which one of the hydroxy groups is protected with an enzyme-cleavable group to remove the enzyme-cleavable group. The dihydroxyaromatic compound undergoes reaction with a heterocyclic enol phosphate compound in the presence of oxygen to generate chemiluminescence. Preferred protected dihydroxyaromatic compound have formula II wherein one of the hydroxy groups of a dihydroxyaromatic compound, I, is protected with a group cleavable by a hydrolytic enzyme. Protected dihydroxyaromatic compounds useful in these methods comprise compounds of formula II:

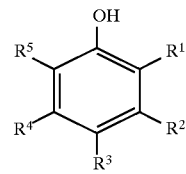

wherein one of $R^1$ or $R^3$ is an OX group wherein X is a group which is removable by a hydrolytic enzyme, the other one of $R^1$ or $R^3$ and $R^2$, $R^4$ and $R^5$ are each independently selected from hydrogen, alkyl, alkoxy, alkenyl, alkynyl, aryl, aralkyl, amino, aminoalkyl, carboxyl —C(=O)OH, carboxyl ester —C(=O)OR$^6$, formyl —C(=O)H, alkylcarboxy —OC(=O)R$^6$, arylcarboxy —OC(=O)R$^9$ and halogen groups wherein pairs of adjacent groups, when taken together, can complete a five or six-membered aliphatic or aromatic ring and wherein $R^6$ is a lower alkyl group, wherein $R^7$ and $R^8$ are each H or a lower alkyl group and wherein $R^9$ is an aryl ring group.

The X group in the protected dihydroxy aromatic compounds of the present invention can be any group which can be cleaved by a hydrolytic enzyme. Hydrolytic enzymes are those enzymes classified in Class E.C. 3.1 or 3.2 of the enzyme classification system and include broadly phosphatase, phosphodiesterase, nuclease, glycosidase, lipase and esterase enzymes. Specific examples include acid phosphatase, alkaline phosphatase, phosphodiesterase, phospholipase, β-D-galactosidase, β-glucuronidase, β-glucosidase, lactase, carboxyl esterase, and acetylcholinesterase. Possible O—X groups include any chemical leaving group which is stable under the conditions of use and can be cleaved by reaction with an enzyme, including without limitation alkyl or aryl carboxyl ester, inorganic oxyacid salt including phosphate and sulfate, and oxygen-pyranoside including α- and β-D-galactoside, α- and β-glucuronide, and α- and β-glucoside groups and the like as are apparent to those of ordinary skill in the art. Preferred hydrolytic enzymes are alkaline phosphatase, acid phosphatase, β-D-galactosidase, β-glucuronidase and β-glucosidase.

Formation of the dihydroxyaromatic compound by reaction of a compound of formula II with a hydrolytic enzyme can be performed in the presence or absence of the heterocyclic enol phosphate compound (III) so that the formation of I and the generation of chemiluminescence can proceed concurrently or consecutively.

In one method of producing chemiluminescence, the protected dihydroxyaromatic compound is reacted with an appropriate hydrolytic enzyme in the presence of a heterocyclic enol phosphate compound in a buffer. The pH is maintained at a value which is conducive to enzyme activity and the chemiluminescent reaction usually between about pH 8 and 10 and preferably between about pH 9 and 10. Conducting the reaction in this manner results in a continuous chemiluminescence signal.

In an alternate mode of performing the present chemiluminescent reactions, the protected dihydroxyaromatic compound is reacted with a hydrolytic enzyme in a buffer or on a solid surface at a first pH, preferably in the range 5.0–9.5, for a first period of time, preferably ranging from a few seconds to several min. Then this solution or a measured portion thereof is reacted with a second solution containing the heterocyclic enol phosphate compound and optionally an anionic surfactant, and the light measured either by measuring the peak intensity, or integrating for a fixed time period or until light emission has ceased. The pH of the second solution should be ≧8 and preferably between 9 and 10 and will typically be a buffer solution.

This mode of generating the chemiluminescence may be advantageous in assays in which a large number of samples is processed simultaneously for measurement at a later time. This two-step mode is also useful for measuring hydrolytic enzymes with optimum activity at acidic to neutral pH (5–8) such as β-galactosidase or acid phosphatase. An optional step which can also be incorporated into such a chemiluminescent reaction or assay is to add an enzyme inhibitor to the reaction system after the first period of time to stop all further enzyme action.

It will be appreciated that the selection between these two reaction modes will be governed by various factors and the particular use or application. Nevertheless both modes are effective. For enzymes with an acidic pH optimum it may be advantageous to carry out the reaction in two discrete steps, each at an optimum pH, temperature, ionic strength, buffer salt, etc.

In producing chemiluminescence from the reaction of compound II with a hydrolytic enzyme in the presence of a heterocyclic enol phosphate, the reaction is generally performed at a temperature between 5° C. and 50° C., preferably between 20° C. and 40° C. in an aqueous buffer solution at a pH between 7 and 10.5, preferably between 8.5 and 10. Compound III is used at a concentration between 1 $\mu$M and 20 mM, preferably between 50 $\mu$M and 5 mM. Compound II is used at a concentration between 1 $\mu$M and 20 mM, preferably between 50 $\mu$M and 5 mM.

An anionic surfactant can also be employed in the chemiluminescent reaction of the present invention. Anionic surfactants function decreasing background chemiluminescence from the heterocyclic enol phosphate in the absence of the dihydroxyaromatic compound. When used, anionic surfactants will be employed in an amount between 0.01 and 5 mg/mL in the final reaction solution, more preferably between 0.1 and 2.5 mg/mL. Anionic surfactant enhancers include alkyl sulfates and alkyl sulfonates. More extensive lists of exemplary structures of each category of surfactant can be found in any standard treatise on surfactants. Preferred surfactants are $C_{10}$–$C_{20}$ alkyl sulfates such as sodium dodecyl sulfate, SDS.

An important use of the enzymatic chemiluminescent methods is for detecting the presence or amount of an analyte in an assay procedure by a chemiluminescent reaction. The method comprises the steps of contacting a sample suspected of containing the analyte with a chemiluminescent compound of the present invention and a hydrolytic enzyme, detecting the light produced in a qualitative method and, if quantitation is desired, relating the amount of light produced to the amount of the analyte. The relationship between light intensity and amount of analyte can be easily discerned by constructing a calibration curve with known amounts of the analyte. The chemiluminescent compound is typically used in a concentration of about $10^{-5}$M to about $10^{-2}$M, preferably between about $10^{-4}$M and about $10^{-3}$M. The hydrolytic enzyme is preferably below about $10^{-9}$M when detected in a solution.

There are several categories of analytes which can be assayed by the present methods. These include hydrolytic enzymes, in which case it would be unnecessary to add additional hydrolytic enzyme. For example, when the hydrolytic enzyme is alkaline phosphatase, such a determination may find use e.g. in measuring the level of alkaline phosphatase in blood serum as an indication of the status of a patient's liver function or as an index of certain disease conditions. Measurement of prostatic acid phosphatase is also useful as a clinical diagnostic index of prostate cancer.

Detection and measurement of enzyme activity by a chemiluminescent assay of the present invention will find use in gene expression assays. β-Galactosidase, β-glucuronidase and alkaline phosphatase, in particular an isozyme produced in the placenta which is excreted, are useful as reporter genes (J. Alam, J. Cook, Anal. Biochem. 188, 245–54 (1990)). In this type of assay, a gene responsible for expression of a reporter enzyme is cloned into the genetic material of an organism via a plasmid in the vicinity of a promoter or enhancer sequence. The effect of the promoter or enhancer sequence on transcriptional activity is gauged by measuring the level of production of reporter enzyme.

Analyte used in this context also includes inhibitors of hydrolytic enzymes. Inhibitors include compounds which act reversibly by competing with a second substrate such as a protected dihydroxyaromatic compound as well as those inhibitors which act irreversibly by deactivating the enzyme. For example, inhibitors of alkaline phosphatase include inorganic phosphate, levamisole, tetramisole and other imidazo[1,2-b]thiazoles, L-phenylalanine and L-homoarginine and are identified in R. B. McComb, G. N. Bowers, S. Posen in *Alkaline Phosphatase*, Plenum Press, New York 1979, pp. 268–275, 332–334, 394–397, 410–413. Inhibitors of other hydrolytic enzymes are generally known to one of skill in the art of enzyme assays. When using the chemiluminescent reaction of the present invention for detecting an enzyme inhibitor, the appropriate hydrolytic enzyme is reacted with a compound of formula II to form a dihydroxyaromatic compound I which is reacted with a heterocyclic enol phosphate III in the presence and absence of the inhibitor substance and the results are compared to determine the presence or amount of the inhibitor. The difference in the chemiluminescence emitted is indicative of the presence of the inhibitor.

Analyte used in this context further includes various classes of organic and biological molecules which can be labeled with a hydrolytic enzyme or can be specifically detected through enzyme-labeled specific binding partners. The enzyme can be incorporated directly as a label on the analyte binding compound. Alternately the analyte binding compound may be bound to at least one enzyme-labeled specific binding substance for the analyte binding compound. Exemplary of this format would be a nucleic acid hybridization assay using an enzyme-labeled detection oligonucleotide. Alternately the analyte binding compound can be labeled with at least one second specific binding substance, e.g. biotin, which is then bound to a enzyme-labeled binding partner for the second specific binding substance, e.g. avidin.

Biological molecules which can be conjugated to one or more molecules of a hydrolytic enzyme include DNA, RNA, oligonucleotides, antibodies, antibody fragments, antibody-DNA chimeras, antigens, haptens, proteins, lectins, avidin, streptavidin and biotin. Complexes including or incorporating hydrolytic enzymes such as liposomes, micelles, vesicles and polymers which are functionalized for attachment to biological molecules can also be used in the methods of the present invention.

Techniques for performing enzyme assays are well known. With the guidance provided by the examples as taught herein, variations of procedures for preparing samples, determining appropriate quantities and ratios of reagents, reaction times, constructing calibration curves and the like will be within the ability of one of ordinary skill in the art to devise as a matter of routine experimentation.

Since the reaction is catalyzed by the hydrolytic enzyme, exceedingly small quantities of the enzyme are sufficient to produce a detectable amount of light. Sensitivities of <1 amol ($1\times10^{-18}$ mol) have been achieved. The ability to detect such small amounts of hydrolytic enzymes make the present chemiluminescent technology suitable for analyses of many types of analytes using enzyme-linked assays. Such analyses and assays require the ability to detect small quantities of hydrolytic enzymes due to low abundance of the analyte in the sample to be analyzed or to limited sample quantity. In this type of assay, alkaline phosphatase is conjugated to one member of a specific binding pair. An example is chemiluminescent enzyme-linked immunoassays, such as the so-called enzyme-linked immunosorbent assay or ELISA. Such assays are commonly used in manual format as well as on automated multi-test immunoassay systems. In a typical immunoassay, the analyte hapten, antigen or antibody is assayed by detecting the presence or amount of an enzyme-labeled specific binding partner for the analyte or an enzyme-labeled analog of the analyte. Various assay formats and the protocols for performing the immunochemical steps are well known in the art. These assays fall broadly into two categories. Competitive assays feature an immunological binding of a specific antibody with the analyte and an analyte analog, e.g. a detectably labeled analyte molecule. Sandwich assays result by the sequential or simultaneous binding of two antibodies, one of which is detectably labeled, with the analyte. The detectable enzyme-labeled binding pair so formed can be assayed with the compounds and methods of the present invention. Measurement can be performed with enzyme-labeled species attached to a solid surface or support including beads, tubes, microwells, magnetic particles, test strips, membranes and filters such as are in common use in the art. The detectable enzyme-labeled species can also be present free in solution or enclosed within an organized assembly such as a liposome in which case a lytic agent is employed to lyse the liposome and free the detectable enzyme.

Another exemplary use is the detection of proteins by the technique of Western blotting. A sample containing a protein of interest as the analyte is subject to electrophoretic separation. The separated proteins are transferred to a blotting membrane by capillary action or with the aid of an electric field. Such transferred protein is typically detected with a specific primary antibody and an enzyme-labeled secondary antibody which recognizes and binds to the primary antibody. Visualization of marker enzyme activity reflects the presence of the analyte protein. To adapt the methods of the present invention for Western blotting, a secondary antibody conjugated to a hydrolytic enzyme such as alkaline phosphatase or β-galactosidase can be employed and enzyme activity measured with chemiluminescence using a compound of formula II as the enzyme substrate and a compound of formula III as the chemiluminescent reagent. Variations on this technique such as using biotinylated antibodies and avidin-enzyme conjugates are considered within the scope of assays able to be performed using the inventive methods.

In addition to the aforementioned antigen-antibody, hapten-antibody or antibody-antibody pairs, specific binding pairs also can include complementary oligonucleotides or polynucleotides, avidin-biotin, streptavidin-biotin, hormone-receptor, lectin-carbohydrate, IgG-protein A, nucleic acid-nucleic acid binding protein and nucleic acid-anti-nucleic acid antibody.

A particularly useful application of the present detection methods is the detection of nucleic acids by the use of enzyme-labeled nucleic acid probes. Methods for analysis and chemiluminescent detection of nucleic acids using enzyme-labels, for example, solution hybridization assays, DNA detection in Southern blotting, RNA by Northern blotting, DNA sequencing, DNA fingerprinting, colony hybridizations and plaque lifts are all well established techniques. The enzyme label (e.g. AP or β-gal) can be present as a direct conjugate with a probe oligonucleotide or capture oligonucleotide or it can be incorporated through indirect linking means using art-known methods. Examples of indirect linking means include using hapten-labeled oligonucleotides and anti-hapten-enzyme conjugates or biotinylated oligonucleotides and avidin-enzyme conjugates. Such nucleic acid assays can be performed on a blotting membrane or in solution using oligonucleotides attached to solid surfaces including beads, tubes, microwells, magnetic particles, test strips such as are known in the art.

In another aspect, the present invention relates to a reagent composition for producing chemiluminescence by reaction with a hydrolytic enzyme comprising a protected dihydroxyaromatic compound of formula II to produce the dihydroxyaromatic compound of formula I which in the presence of a compound of formula III and oxygen produces chemiluminescence. The reagent composition comprises an aqueous buffer with a pH in the range 7–10.5, a compound of formula II at a concentration of 0.001–20 mM and a compound of formula III at a concentration of 0.001–20 mM. Formulations for chemiluminescent reaction with a hydrolytic enzyme can further comprise a metal salt such as a magnesium or zinc at a concentration of 0.01–10 mM for increasing or sustaining the activity of the enzyme.

In a preferred embodiment the composition additionally comprises an anionic surfactant at a concentration preferably between 0.01 and 5 mg/mL in the final reaction solution, more preferably between 0.1 and 2.5 mg/mL.

A preferred reagent composition for producing chemiluminescence in a one-step process by reaction with a hydrolytic enzyme comprises an aqueous buffer with a pH in the range of 8–10, a protected dihydroxyaromatic compound of formula II at a concentration of about 0.05–5 mM, an acridan phosphate of formula IIIc at a concentration of about 0.05–5 mM and optionally, an anionic surfactant at a concentration preferably between 0.1 and 2.5 mg/mL. In a more preferred composition, the protected dihydroxyaromatic compound of formula II has the formula:

wherein X is the group removable by the hydrolytic enzyme.

In order to more fully describe the various aspects of the present invention, the following examples describing compounds, methods of preparation, compositions and methods of use are presented. The examples are to be considered illustrative and do not limit the scope of the invention.

EXAMPLES

1. Synthesis of Acridan Derivative 1

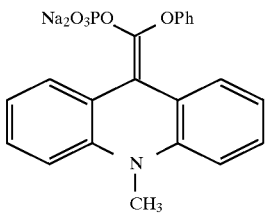

1 a. Phenyl acridine-9-carboxylate. Acridine-9-carboxylic acid (1 g, 4.1 mmol) was suspended in thionyl chloride (5 mL) and the reaction mixture was refluxed for 3 h. The solvent was removed under reduced pressure leaving a yellow solid which was dissolved in $CH_2Cl_2$ and pyridine (350 µL) under argon. This solution was cooled in an ice bath and a solution of phenol (0.78 g, 8.2 mmol) in $CH_2Cl_2$ was added dropwise. The reaction mixture was stirred overnight at room temperature. After evaporation of solvent, the residue was redissolved in ethyl acetate and washed with water. The organic layer was dried over $MgSO_4$ and concentrated to obtain a crude material which was chromatographed on silica gel (30% ethyl acetate/hexane) to yield the pure product as a yellow solid. $^1$H NMR ($CDCl_3$) δ 7.35–7.57 (m, 5H), 7.63–8.37 (m, 8H).

b. Phenyl 10-methylacridinium-9-carboxylate trifluoromethanesulfonate. Phenyl acridine-9-carboxylate (530 mg, 1.7 mmol) was dissolved in $CH_2Cl_2$ (5 mL) under argon and methyl trifluoromethanesulfonate (1 mL, 8.8 mmol) was added. The solution was stirred overnight at room temperature to yield a thick yellow precipitate. This precipitate was filtered, washed with ether and dried to obtain the product as yellow crystals. $^1$H NMR (acetone-$d_6$) δ 5.22 (s, 3H), 7.47–7.71 (m, 5H), 8.23–9.07 (m, 8H).

c. Phenyl 10-methylacridan-9-carboxylate. Phenyl 10-methylacridinium-9-carboxylate trifluoromethanesulfonate (10 mg, 0.0216 mmol) was suspended in absolute ethanol (10 mL) and the mixture was refluxed for 15 min to obtain a clear solution. Ammonium chloride (88 mg, 1.6 mmol) was added by portions to the solution followed by zinc (108 mg, 1.6 mmol). Addition of zinc caused the yellow color of the solution to disappear immediately. The colorless solution was refluxed for 2 h. TLC of the reaction mixture showed complete conversion to a non polar material. The solution was filtered and precipitate was washed with ethanol (3×20 mL). The filtrate was concentrated to obtain an off-white solid which was redissolved in $CH_2Cl_2$ and washed with water (2×15 mL). The organic layer was dried over $Na_2SO_4$ and concentrated to yield the crude product which was purified by preparative TLC using (30% ethyl acetate:hexane). Pure product was obtained as an off-white solid. $^1$H NMR ($CDCl_3$) δ 3.38 (s, 3H), 5.16 (s, 1H), 6.89–7.37 (m, 13H); $^{13}$C NMR ($CDCl_3$) δ 33.29, 49.72, 112.93, 120.19, 121.36, 125.73, 128.67, 129.16, 129.26, 142.37, 151.04, 170.22.

d. 9-(Phenoxyphosphoryloxymethylidene)-10-methylacridan, bis(cyanoethyl) ester. A three-neck flask was purged with argon and charged with 5 mL of anhydrous THF and diisopropylamine (0.04 mL, 0.29 mmol). The flask was cooled in a dry ice-acetone bath. To this solution was added n-butyl lithium (0.116 mL, 0.29 mmol). After 20 min, a solution of the acridan ester from step (c)(70 mg, 0.22 mmol) in 5 mL of THF was added to this solution and stirring was continued for 30 min at −78° C. Finally a solution of $POCl_3$ (0.027 mL, 0.29 mmol) and pyridine (0.023 mL, 0.29 mmol) in 3 mL of THF was added and the dry ice bath was removed. After 45 min, pyridine (0.039 mL, 0.58 mmol) and 3-hydroxypropionitrile (0.094 mL, 1.16 mmol) was added and stirring maintained over night. Then it was filtered and solvent was removed from the filtrate. The residue was subjected to prep. TLC (80% ethyl acetate/hexane) to give the pure product; $^1$H NMR ($CDCl_3$) δ 2.35–2.54 (m, 4H), 3.47 (s, 3H), 3.79–3.90 (m, 2H), 3.98–4.08 (m, 2H), 6.825–7.45 (m, 12H), 7.80–7.83 (dd, 1H); $^{13}$C NMR ($CDCl_3$) δ 19.12, 19.24, 33.63, 62.19, 62.49, 88.72, 92.82, 112.40, 112.52, 115.83, 116.07, 119.68, 120.44, 120.71, 123.81, 126.69, 128.03, 128.27, 128.58, 130.09, 142.39, 143.06, 165.73, 202.09.

e. 9-(Phenoxyphosphoryloxymethylidene)-10-methylacridan, disodium salt (1). A solution of the bis(cyanoethyl) phosphate compound (2.897 g, 5.77 mmol) in 50 mL of acetone was purged with Ar for 30 min. An Ar-purged solution of 479 mg (12 mmol) of NaOH in 7.5 mL of water was added dropwise and the solution stirred over night. The precipitate which had formed was filtered, washed with 50 mL of Ar-purged acetone and air-dried. The yield was 3.473 g of 1 as a white solid which contained some water. $^1$H NMR ($D_2O$) δ 3.326 (s, 3H), 6.825–7.45 (m, 13H), 7.80–7.83 (d, 1H); $^{13}$C NMR ($D_2O$) δ 32.95, 102.86, 102.92, 112.30, 115.85, 120.68, 121.01, 122.35, 122.41, 122.62, 127.48, 127.66, 128.23, 129.66, 143.17, 143.32, 144.66, 156.01; $^{31}$P NMR ($D_2O$) δ 0.581 (rel. to ext. $H_3PO_4$).

2. Synthesis of Acridan Derivative 2

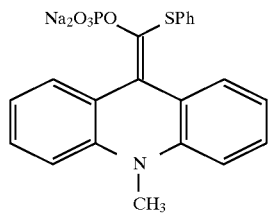

2 a. 9-(Phenythiophosphoryloxymethylidene)-10-methylacridan, bis(cyanoethyl) ester. Phenyl 10-methylacridan-9-thiocarboxylate prepared as decribed in applicant's PCT application WO95/28495 (70 mg, 0.2 mmol) was added to a solution of LDA (0.24 mmol) in THF. After stirring 30 min at −78° C., a solution of $POCl_3$ (25 µL) and pyridine (21 µL) in 4 mL of THF was added. The dry ice bath was removed and stirring continued for 30 min. TLC (30% ethyl acetate/hexane) showed that the starting material was completely reacted. The solution was cooled in an ice bath and treated with pyridine (210 µL) and 3-hydroxypropionitrile (44 µL) in 4 mL of THF. After stirring over night at room temperature, the precipitated pyridine-HCl was filtered away and the reaction solvent evaporated in vacuo. The residue was subjected to prep. TLC (ethyl acetate) from which the product was isolated; $^1$H NMR ($CDCl_3$) δ 2.4–2.6 (m, 4H), 3.521 (s, 3H), 3.8–4 (m, 2H), 4.0–4.1 (m, 2H), 6.9–7.2 (m, 4H), 7.22–7.5 (m, 7H), 7.75–8 (dd, 2H).

b. 9-(Phenylthiophosphoryloxymethylidene)-10-methylacridan, disodium salt (5). A solution of the bis(cyanoethyl) phosphate compound (0.59 g, 1.21 mmol) in 50 mL of acetone was purged with argon for 30 min. An Ar-purged solution of 104 mg (2.6 mmol) of NaOH in 10 mL of water was added dropwise and the solution stirred under argon over night. The precipitate which had formed was suction filtered, washed with 50 mL of Ar-purged acetone and air-dried. The yield was 0.50 g of 5 as a slightly yellow solid which contained a slight amount of acetone. $^1$H NMR (D$_2$O) δ 3.36 (s, 3H), 6.9–7.4 (m, 11H), 7.75–7.8 (d, 1H) , 8.2–8.22 (d, 1H); $^{31}$P NMR (D$_2$O) δ 1.85.

Example 3

Synthesis of Acridan Derivative 3

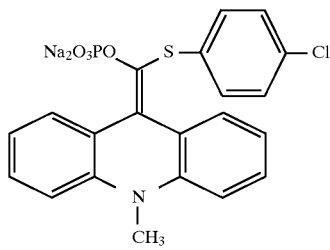

a. 4'-Chlorophenyl acridine-9-thiocarboxylate. 4-Chlorothiophenol (4.75 g) and 7.22 g of acridine-9-carbonyl chloride were dissolved in 100 mL of CH$_2$Cl$_2$ followed by 12.1 mL of pyridine. The reaction mixture became orange-brown. The mixture was stirred overnight at room temperature under argon. After evaporation of solvent, the solids were washed with 100 mL of hexanes, filtered, washed with another 100 mL of hexanes, filtered, and then with a 500 mL of water, filtered and air-dried. The thioester was obtained (8.71 g) as a slightly brownish yellow solid. $^1$H NMR (CDCl$_3$) δ 7.47–7.50 (m, 2H), 7.58–7.67 (m, 4H), 7.81–7.86 (m, 2H), 8.12 (d, 2H), 8.29 (d, 2H).

b. 4'-Chlorophenyl acridan-9-thiocarboxylate. 4'-Chlorophenyl acridine-9-thiocarboxylate (2.0 g) was dissolved in CH$_2$Cl$_2$ (25 mL). The solution was purged with argon and then 3.72 g of zinc powder added followed by 0.45 mL of acetic acid. TLC showed the starting material was consumed in 20 min. The mixture was filtered and the solids washed with CH$_2$Cl$_2$. The combined CH$_2$Cl$_2$ solutions were washed with water (3×50 mL) and dried. A small amount of the product was purified by prep. TLC for analytical characterization. The remainder of the product was used without further purification. $^1$H NMR (CDCl$_3$) δ 5.22 (s, 1H), 6.28 (s, 1H), 6.79–7.31 (m, 12H).

c. 4'-Chlorophenyl 10-methylacridan-9-thiocarboxylate. 4'-Chlorophenyl acridan-9-thiocarboxylate (2.0 g) was dissolved in CH$_2$Cl$_2$ (30 mL) under argon and methyl triflate (6.5 g) was added and stirred over night. The brown solution was evaporated and the crude product purified by column chromatography using 30% ethyl acetate/hexanes. The pure product (1.8 g) was thereby obtained. $^1$H NMR (CDCl$_3$) δ 3.47 (s, 3H), 5.09 (s, 1H), 7.02–7.39 (m, 12H).

d. 9-(4-Chlorophenylthiophosphoryloxymethylidene)-10-methylacridan, bis(cyanoethyl) ester. 4-Chlorophenyl 10-methylacridan-9-thiocarboxylate (0.70 g) in 10 mL of anhydrous THF was added dropwise to a solution of LDA (1.4 eq.) in THF at −78° C. After stirring 60 min at −78° C., the yellow solution was treated with a solution of POCl$_3$ (0.517 g) and pyridine (1.52 mL) in 4 mL of THF slowly. The dry ice bath was removed after 30 min and stirring continued for 1 h. The solution became yellow and formed a precipitate.

The mixture was cooled in an ice bath and treated with 3-hydroxypropionitrile (0.89 g) and 1.0 mL of pyridine. The ice bath removed after the addition was complete. After stirring over night at room temperature, the precipitated pyridine-HCl was filtered off and washed with THF. The combined filtrates were evaporated in vacuo and the brown material obtained was dissolved in ethyl acetate and washed with 4×25 mL of water. The ethyl acetate solution was dried and concentrated. The residue was separated by column chromatography using 80–100% ethyl acetate/hexanes from which the 0.325 g of the product was isolated; $^1$H NMR (CDCl$_3$) δ 2.48–2.64 (m, 4H), 3.53 (s, 3H), 3.86–4.16 (m, 4H), 6.94–7.94 (m, 12H); $^{31}$P NMR (D$_2$O) δ−9.48 (p).

e. 9-(4-Chlorophenylthiophosphoryloxymethylidene)-10-methylacridan, disodium salt (3). A solution of the bis (cyanoethyl) phosphate compound (0.325 g) in 10 mL of acetone was purged with argon. A solution of 2.5M NaOH (473 μL) was added followed by an additional 500 μL of water. The solution was stirred under argon over night. The precipitate which had formed was suction filtered and air-dried. The mother liquor was found to contain the mono (cyanoethyl)-protected compound (140 mg). A second crop of the disodium salt was obtained by repeating the NaOH deprotection. $^1$H NMR (D$_2$O) δ 3.35 (s, 3H), 6.92–7.36 (m, 10H), 7.78 (d, 1H), 8.20 (d, 1H); $^{31}$P NMR (D$_2$O) δ 1.22 (s).

Example 4

Synthesis of Acridan Derivative 4

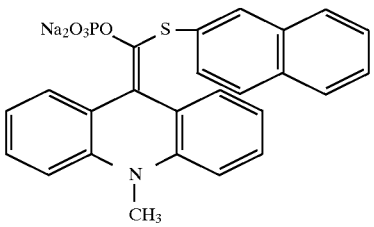

a. Naphthyl acridine-9-thiocarboxylate. 2-Naphthalenethiol (48.81 g) and the acridine-9-carbonyl chloride prepared from 65.17 g of acridine-9-carboxylic acid were dissolved in 100 mL of CH$_2$Cl$_2$ followed by the addition of 120 mL of pyridine. The mixture was stirred overnight at room temperature under argon. After evaporation of solvent, the solids were washed with 500 mL of hexanes, filtered, washed with another 500 mL of hexanes, filtered, and then washed with 600 mL of water, filtered and air-dried overnight. The thioester was dissolved in 1500 ml of CH$_2$Cl$_2$, dried over sodium sulfate, filtered, and dried in vacuo. The thioester was obtained (94.67 g) as a brown solid. $^1$H NMR (CDCl$_3$) δ 7.54–8.00 (m, 11H), 8.17–8.31 (m, 4H).

b. Naphthyl 10-methylacridinium-9-thiocarboxylate triflate. Naphthyl acridine-9-thiocarboxylate (26.38 g) was suspended in CH$_2$Cl$_2$ (200 mL). Methyl trifluoromethanesulfonate (24.5 ml) was added and the mixture left to stir overnight. The mixture was filtered and the solids washed with CH$_2$Cl$_2$ (300 ml) and hexanes (500 ml). After air drying, the product (28.83 g) was obtained as a yellow solid. $^1$H NMR (acetone-d$_6$) δ 5.20 (s, 3H), 7.66–7.75 (m, 2H), 7.88–7.92 (m, 1H), 8.03–8.09 (m, 2H), 8.15 (d, 1H), 8.26 (t, 2H), 8.48 (s, 1H), 8.61–8.68 (m, 2H), 8.80 (d, 2H), 9.03 (d, 2H).

c. Naphthyl 10-methylacridan-9-thiocarboxylate. Naphthyl 10-methylacridinium-9-thiocarboxylate triflate (65.50 g) was suspended in CH$_2$Cl$_2$ (1000 mL) under argon and glacial acetic acid (21.2 ml) and zinc (40.43 g) were added. After stirring overnight, TLC showed the disappearance of the starting material and the formation of a new product. The reaction mixture was filtered through a bed of silica gel and the CH$_2$Cl$_2$ removed in vacuo. The slightly yellow solid obtained was stirred in isopropanol (500 ml), filtered, washed with 500 ml more isopropanol, and allowed to air dry. The pure product (46.36 g) was thereby obtained. $^1$H NMR (CDCl$_3$) δ 3.47 (s, 3H) , 5.13 (s, 1H) , 7.00–7.06 (m, 4H), 7.25–7.49 (m, 7H), 7.70–7.79 (m, 4H).

d. 9-(Naphthylthiophosphoryloxymethylidene)-10-methyl-acridan, bis(cyanoethyl) ester. Naphthyl 10-methylacridan-9-thiocarboxylate (17.32 g) in 600 mL of anhydrous THF was added dropwise to a solution of LDA (1.25 eq.) in THF at −78° C. After stirring 90 min at −78° C., the orange-brown solution was treated with a solution of POCl$_3$ (20.80 g) and pyridine (50 mL) in 150 mL of THF slowly. The dry ice bath was removed after 60 min and stirring continued for 1 h. The solution became brown and formed a precipitate.

The mixture was treated with 3-hydroxypropionitrile (27.8 ml). After stirring over night at room temperature, the precipitated pyridine-HCl was filtered off and washed with THF. The combined filtrates were evaporated in vacuo and the brown oil obtained was separated by column chromatography using 50–100% ethyl acetate/hexanes from which the product was isolated. The yellow oil was dissolved in CH$_2$Cl$_2$ (300 ml), washed with water (450 ml), dried over sodium sulfate, filtered, and dried in vacuo. This yielded the product (17.76 g) as a yellow solid. $^1$H NMR (CDCl$_3$) δ 2.33–2.53 (m, 4H), 3.53 (s, 3H), 3.82–4.06 (m, 4H), 6.93 (t, 1H), 7.03 (d, 1H), 7.10–7.18 (m, 2H), 7.25–7.55 (m, 5H), 7.79–7.92 (m, 5H), 8.02 (d, 1H); $^{31}$P NMR (CDCl$_3$) δ−9.69 (p) (rel. to ext. H$_3$PO$_4$).

e. 9-(Naphthylthiophosphoryloxymethylidene)-10-methyl-acridan, disodium salt (4). A solution of the bis(cyanoethyl) phosphate compound (17.28 g) in 200 mL of acetone was purged with argon. A solution of NaOH (2.76 g) in 50 ml of water was added and the solution was stirred under argon over night. The precipitate which had formed was suction filtered washed with 20% water in acetone (300 ml) and dried under vacuum. The product (15.07 g) was obtained as a light yellow solid. $^1$H NMR (D$_2$O) δ 3.22 (s, 3H), 6.67 (d, 1H), 6.87 (t, 1H), 7.01 (t, 1H), 7.08–7.15 (m, 2H), 7.23 (d, 1H), 7.31–44 (m, 3H), 7.51 (s, 1H), 7.59 (d, 2H), 7.73 (d, 1H), 7.86 (d, 1H), 8.25 (d, 1H); $^{31}$P NMR (D$_2$O) δ 1.30 (s).

Example 5

Additional Heterocyclic Enol Phosphates Prepared

The following compounds of formula IV have also been prepared and function in the chemiluminescent reactions of the present invention.

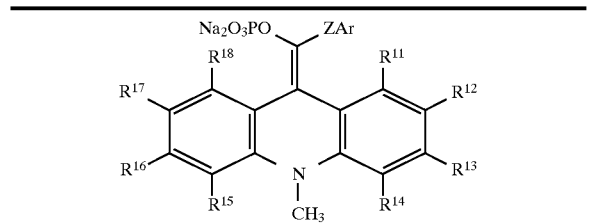

| Compound | R$^{11}$–R$^{18}$ | Z | Ar |
|---|---|---|---|
| 5 | all H | O | 3,5-difluorophehyl |
| 6 | R$^{13}$ = OCH$_3$ | O | phenyl |
| 7 | R$^{13}$ = Cl | O | 2,6-dimethylphenyl |
| 8 | R$^{15}$–R$^{16}$ = —CH=CH—CH=CH— | O | phenyl |
| 9 | all H | O | 3,5-bis(carboxymethyl) |
| 10 | all H | S | 4-fluorophenyl |
| 11 | all H | S | 4-methoxyphenyl |

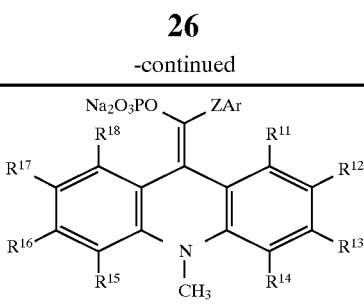

| Compound | R$^{11}$–R$^{18}$ | Z | Ar |
|---|---|---|---|
| 12 | all H | S | 2,6-dimethylphenyl |
| 13 | R$^{12}$, R$^{17}$ = F | S | phenyl |
| 14 | all H | S | trifluoroethyl |

R$^{11}$–R$^{18}$ are H unless otherwise indicated. Compounds 6–8 were obtained as a mixture of double bond isomers. Each of compounds 5–14 were prepared by the general synthetic methods described in Examples 1–4. In addition compounds of the formulas:

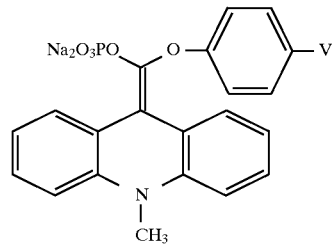

wherein V is t-butyl, CH$_3$, OCH$_3$, F, Cl, Br, I, COCH$_3$, CN and NO$_2$ as well as compounds of the formula:

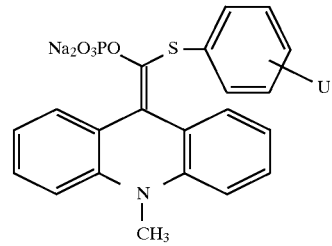

wherein U is p—I, p—CH$_3$, m—OCH$_3$, o—Cl, m—Cl, o—Br, m—Br, p—Br and p—NO$_2$ as well as compounds of this formula having a 3,4-dichloro-, 2,5-dichloro- and 2,6-dichlorophenyl group have been prepared and produce chemiluminescence when reacted with a dihydroxyaromatic compound.

Example 6

Preparation of Protected Dihydroxyaromatic Compound 4-Hydroxyphenyl phosphate, disodium salt Hydroquinone was protected as the monobenzoate ester in 62% yield by reaction with benzoyl chloride and pyridine in CH$_2$Cl$_2$ at 0° C. The ester was phosphorylated with excess POCl$_3$ in pyridine at 0° C. The dichlorophosphate derivative was reacted with 10 eq. of 3-hydroxypropionitrile to produce the bis(cyanoethyl phosphate) in 89% yield. The cyanoethyl and benzoyl, protecting groups were hydrolyzed with aq. NaOH/acetone at room temperature over night. The precipitated product was dissolved in methanol and precipitated with acetone to produce 4-hydroxyphenyl phosphate as the disodium salt. $^1$H NMR (D$_2$O) δ 6.56 (d, 1H), 6.92 (t, 1H)

Example 7

Preparation of Protected Dihydroxyaromatic Compound 2-Hydroxyphenyl phosphate, disodium salt Catechol was protected as the monobenzoate ester in 62% yield by reaction with benzoyl chloride and pyridine in CH$_2$Cl$_2$ at 0° C. The ester was phosphorylated with excess POCl$_3$ and pyridine in CH$_2$Cl$_2$ at 0° C. The dichlorophosphate derivative was reacted with 10 eq. of 3-hydroxypropionitrile to produce the bis(cyanoethyl phosphate) in 90% yield. The cyanoethyl and benzoyl protecting groups were hydrolyzed with aq. NaOH/acetone at room temperature over night. The precipitated product was dissolved in methanol, precipitated with acetone and the solid washed again with methanol to produce 2-hydroxyphenyl phosphate as the disodium salt. $^1$H NMR (D$_2$O) δ 6.56–6.61 (m, 1H), 6.68–6.71 (d, 1H), 6.82–6.87 (m, 1H), 7.19–7.22 (d, 1H).

Example 8

Preparation of Protected Dihydroxyaromatic Compound 4-Hydroxy-2,3,5,6-tetrafluorophenyl phosphate, disodium salt 2,3,5,6-Tetrafluorohydroquinone was protected as the mono(t-butyldimethylsilyl) ether in 46% yield by reaction with t-butyldimethylsilyl chloride and imidazole in DMF over night at room temperature. After chromatographic purification (10% ethyl acetate/hexane), the silyl ether was phosphorylated with excess POCl$_3$ in pyridine at 0° C. The dichlorophosphate derivative was reacted with 10 eq. of 3-hydroxypropionitrile to produce the bis(cyanoethyl phosphate) derivative which had also been desilylated in 55% yield after column chromatography (75–100% ethyl acetate in hexane). The cyanoethyl protecting group was hydrolyzed with aq. NaOH/acetone at room temperature for 2 days. The precipitated product was dissolved in methanol and precipitated with acetone to produce the disodium phosphate salt. $^{31}$P NMR (CD$_3$OD) δ 4.244; $^{19}$F NMR (CD$_3$OD) δ −169.02 (d, 2F), −161.16 (d, 2F)

Example 9

Preparation of Protected Dihydroxyaromatic Compounds 2- and 3-Chloro-4-hydroxyphenyl phosphate, disodium salt 2-Chlorohydroquinone, 20 g (Aldrich, Milwaukee, Wis. was recrystallized by dissolving in 350 mL of warm 10% ethyl acetate/CH$_2$Cl$_2$, filtered and added to 1.5 L of hexane. After cooling to 4° C. over night, 11 g of off white solid was collected. The purified 2-chlorohydroquinone was monoacetylated with acetyl chloride/Apyridine in CH$_2$Cl$_2$ at ice temperature to produce a mixture of the isomeric monoacetates and the diacetate. The mixture was phosphorylated with excess POCl$_3$ in pyridine at 0° C. The reaction product was reacted with excess 2-cyanoethanol to produce a 4:1 mixture of isomeric bis(cyanoethyl phosphate) derivatives which were separated from the diacetate by column chromatography (30% ethyl acetate/hexane). The acetate and cyanoethyl protecting groups were hydrolyzed with aq. NaOH/acetone (3 eq. of NaOH) at 0° C. for 19 h. The precipitated product was dissolved in methanol and precipitated with acetone to produce the isomeric disodium phosphate salts. $^1$H NMR (D$_2$O) δ 6.56–7.19 (m, 3H); $^{31}$P NMR (D$_2$O) δ 1.36, 1.39.

Example 10

Preparation of Protected Dihydroxyaromatic Compound 4-Hydroxyphenyl β-D-galactopyranoside Hydroquinone was reacted with α-bromogalactose tetraacetate (1.5 eq.) in ethanol/aq. NaOH at room temperature for 2 days in a light-shielded vessel. Sodium ethoxide (5 eq.) was added and the solution concentrated after one hour. The residue was partitioned between water and ethyl acetate. The water layer was evaporated and the product purified chromatopgraphically (30% methanol/CH$_2$Cl$_2$) on silica. $^1$H NMR (CD$_3$OD) δ 3.57–3.88 (m, 6H), 4.68 (d, 1H), 6.68 (d, 2H), 6.96 (d, 2H).

Example 11

Preparation of Protected Dihydroxyaromatic Compound 4-Hydroxyphenyl β-D-glucuronide Hydroquinone (10 g) was converted to the monobenzoate ester by reaction with benzoyl chloride and pyridine in CH$_2$Cl$_2$. The yield was 7 g of the ester. $^1$H NMR (CDCl$_3$) δ 4.880 (s, 1H), 6.87 (d, 2H), 7.08 (d, 2H), 7.52 (t, 2H), 7.64 (t, 1H), 8.20 (d, 2H).

The latter (200 mg) was deprotonated with aq. NaOH in acetone and converted to the β-glucuronide ethyl ester derivative by reaction with ethyl α-D-bromoglucuronate in absolute ethanol. Purification by prep. TLC afforded 50 mg of the doubly protected compound. $^1$H NMR (CD$_3$OD) δ 1.290 (t, 3H), 3.601–3.780 (m, 3H), 4.146–4.258 (m, 3H), 4.64 (br s, 2H), 4.86 (br s, 1H), 5.192 (d, 1H), 7.187–7.285 (m, 4H), 7.635 (t, 2H), 7.767 (t, 1H), 8.208 (d, 2H).

A 50 mg sample of the latter compound was hydrolyzed with aq. NaOH in acetone to saponify the benzoate ester and ethyl ester groups. The precipitated product (16 mg) was filtered and dried. $^1$H NMR (CD$_3$OD) δ 3.4–3.5 (m, 3H), 3.64 (d, 1H), 4.65 (d, 1H), 6.53 (d, 2H), 6.87 (d, 2H).

Example 12

Evaluation of Dihydroxyaromatic compounds

Several dihydroxyaromatic compounds were screened to determine their general effectiveness in inducing the chemiluminescent reaction of 1. Stock solutions of the test compounds (2×10$^{-4}$M in ethanol/10% DMSO or DMSO) were prepared. A 5 μL aliquot of each was placed into a well of a 96 well microplate. To each well 95 μL of a solution containing 0.66 mM compound 1, in 0.2M 2-methyl-2-amino-1-propanol buffer, pH 9.6, 0.88 mM Mg$^{2+}$ and 0.1% SDS was added. Light intensity was scanned in all wells for 30 min. The maximum intensity and time to maximum were determined for each test well.

| Dihydroxyaromatic compound | Time to max | Max S/B |
|---|---|---|
| 2-Chlorohydroquinone (DHA-1) | 6 | >32,000 |
| Hydroquinone (DHA-2) | 6 | 20,000 |
| 2-Phenylhydroquinone (DHA-3) | 7.5 | 10,200 |

-continued

| Dihydroxyaromatic compound | Time to max | Max S/B |
|---|---|---|
| 3,3,3',3'-Tetramethyl-1,1'-spirobisindane-5,5',6,6'-tetrol (DHA-4) | ≧30 | 3,000 |
| 2,3,5,6-Tetrafluorohydroquinone (DHA-5) | 5 | 2,800 |
| 2-Methylhydroquinone (-DHA-6) | 15 | 800 |
| 2-Methoxyhydroquinone (DHA-7) | 5 | 480 |
| Catechol (DHA-8) | ≧30 | 260 |
| 1,2-Dihydroxyanthracene (DHA-9) | 7 | 160 |
| 7,8-Dihydroxy-6-methoxycoumarin (DHA-10) | ≧30 | 150 |
| 1-Methyl-6,7-dihydroxy-1,2,3,4-tetrahydroisoquinoline (DHA-11) | ≧30 | 50 |
| 4-Amino-resorcinol (DHA-12) | ≧30 | 45 |
| 1,4-Dihydroxynaphthalene (DHA-13) | ≧30 | 40 |
| 9,10-Bis(4-hydroxyphenyl)anthracene (DHA-14) | 15 | 24 |
| 1,2,4-Trihydroxybenzene (DHA-15) | ≧30 | 17 |
| 4-Bromoresorcinol (DHA-16) | 5 | 14 |
| 2,3-Dihydro-9,10-dihydroxy-1,4-anthraquinone (DHA-17) | ≧30 | 12 |
| Ellagic acid (DHA-18) | ≧30 | 9 |
| 2,5-Dihydroxybenzaldehyde (DHA-19) | ≧30 | 6.5 |
| 2,3-Dichloro-5,8-dihydroxy-1,4-naphthoquinone (DHA-20) | 7 | 2 |

Example 13

Kinetic Profile of Chemiluminescence Intensity

The rapid generation of chemiluminescence from a composition containing the acridan phosphate 1 and hydroquinone (DHA-2) is shown in FIG. 1. The reaction mixture comprised 0.66 mM acridan phosphate 1 and 4 µM hydroquinone in 2-methyl-2-amino-1-propanol (221) buffer, 0.2M, pH 9.6 also containing 0.88 mM $MgCl_2$.

Example 14

Chemiluminescent Detection of Acridan Phosphate 2 with DHA-1

The following example illustrates the ability to detect very small quantities of a heterocyclic enol phosphate compound by use of the chemiluminescent reaction with a dihydroxyaromatic compound.

Figure 2:
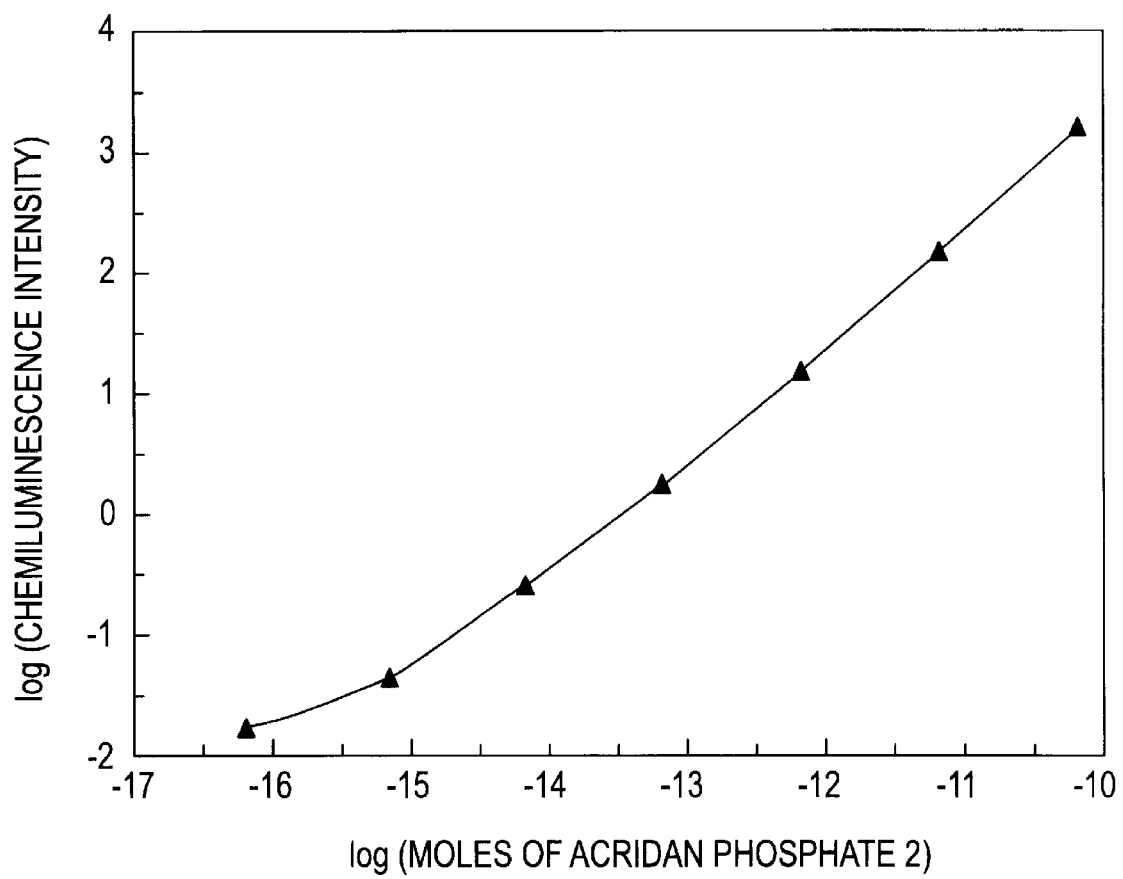
FIG. 2 is a graph relating chemiluminescence intensity to the quantity of acridan phosphate 2. Chemiluminescence emitted by reaction of 100 $\mu$L of a reagent composition consisting of varying amounts of acridan phosphate 2 (dilutions contained between $6.6 \times 10^{-11}$ and $6.6 \times 10^{-17}$ mol) in 0.2M 221 buffer, pH 9.6, 0.88 mM $MgCl_2$, 0.1% SDS with 100 $\mu$L of a 0.01 mM solution of 2-chlorohydroquinone (DHA-1) in water was measured at 2.5 min.

Into each of 3 white microwells was placed a 100 µL aliquot of a solution of acridan phosphate 2 (dilutions contained between $6.6\times10^{-11}$ and $6.6\times10^{-17}$ mol) in 0.2M 221 buffer, pH 9.6, 0.88 mM $MgCl_2$, 0.1% SDS. A 100 µL aliquot of a 0.01 mM solution of 2-chlorohydroquinone (DHA-1) in water was injected into each well and light intensity was measured at 2.5 min. The results shown in FIG. 2 show that light intensity is a direct function of the quantity of the phosphate compound over the entire range tested.

This example demonstrates that the heterocyclic enol phosphate can be detected at concentrations low enough that a suitably functionalized derivative with a linkable group can function as a signal-generating label in a specific binding assay.

Example 15

Reagent for Chemiluminescent Detection of Alkaline Phosphatase

Figure 3:
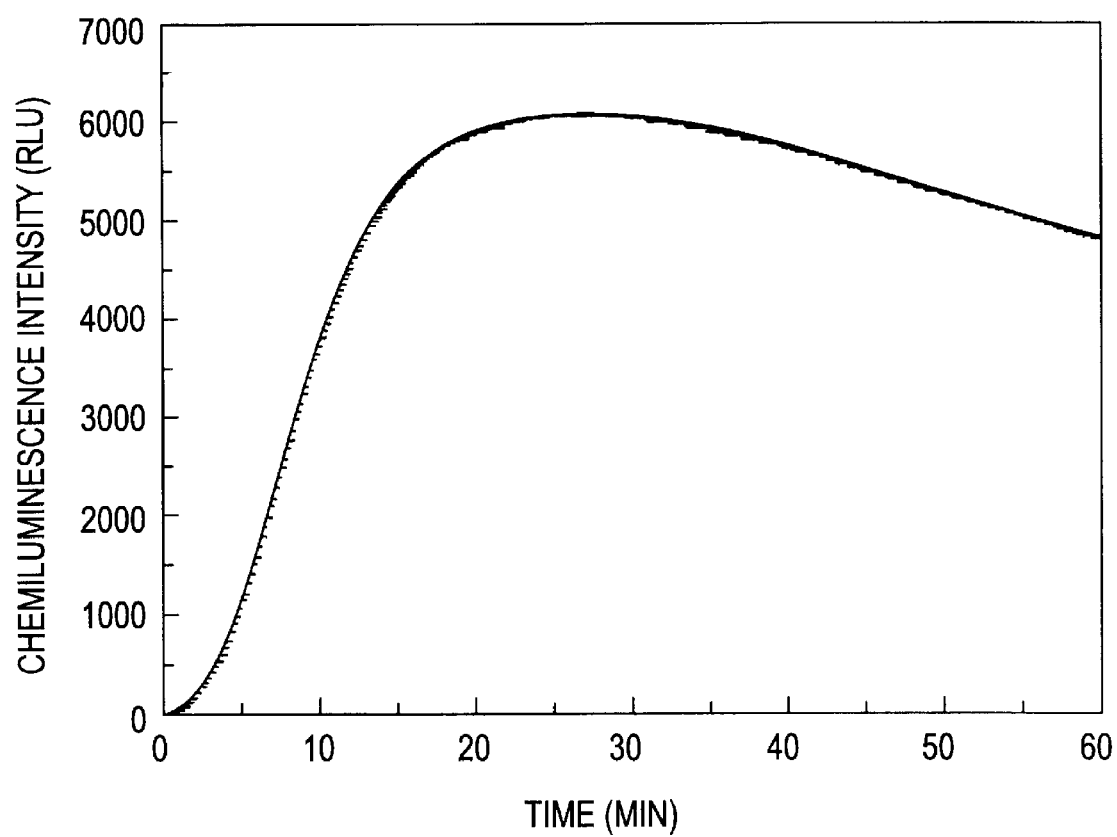
FIG. 3 is a plot showing the time profile of the chemiluminescence intensity emitted by 100 $\mu$L of a reagent consisting of a 0.33 mM solution of acridan phosphate 1 and 1 mm 4-hydroxyphenyl phosphate in 0.1M 221 buffer, pH 9.6 triggered at 25° C. by addition of $8 \times 10^{-17}$ mol of alkaline phosphatase (AP).

An effective reagent composition for chemiluminescent detection of alkaline phosphatase comprised 0.2M 221 buffer, pH 9.6, 0.88 mM $MgCl_2$, 0.33 mM acridan phosphate 1, and 1 mM 4-hydroxyphenyl phosphate. Reaction of 100 µL of this composition with $8\times10^{-17}$ mol of AP at 25° C. in a test tube housed in a Turner TD-20e luminometer produced easily measurable blue chemiluminescence. The time profile of a typical reaction is shown in FIG. 3.

Example 16

Chemiluminescent Detection with Other Heterocyclic Enol Phosphate Compounds

In the manner of the previous Example, compositions containing each of acridan phosphates 2–4 in place of compound 1 were reacted with AP at 25° C. Each produced easily measurable chemiluminescence discernable above the background in the absence of AP.

Example 17

Effect of Concentration of Protected Dihydroxyaromatic Compound

Figure 4:
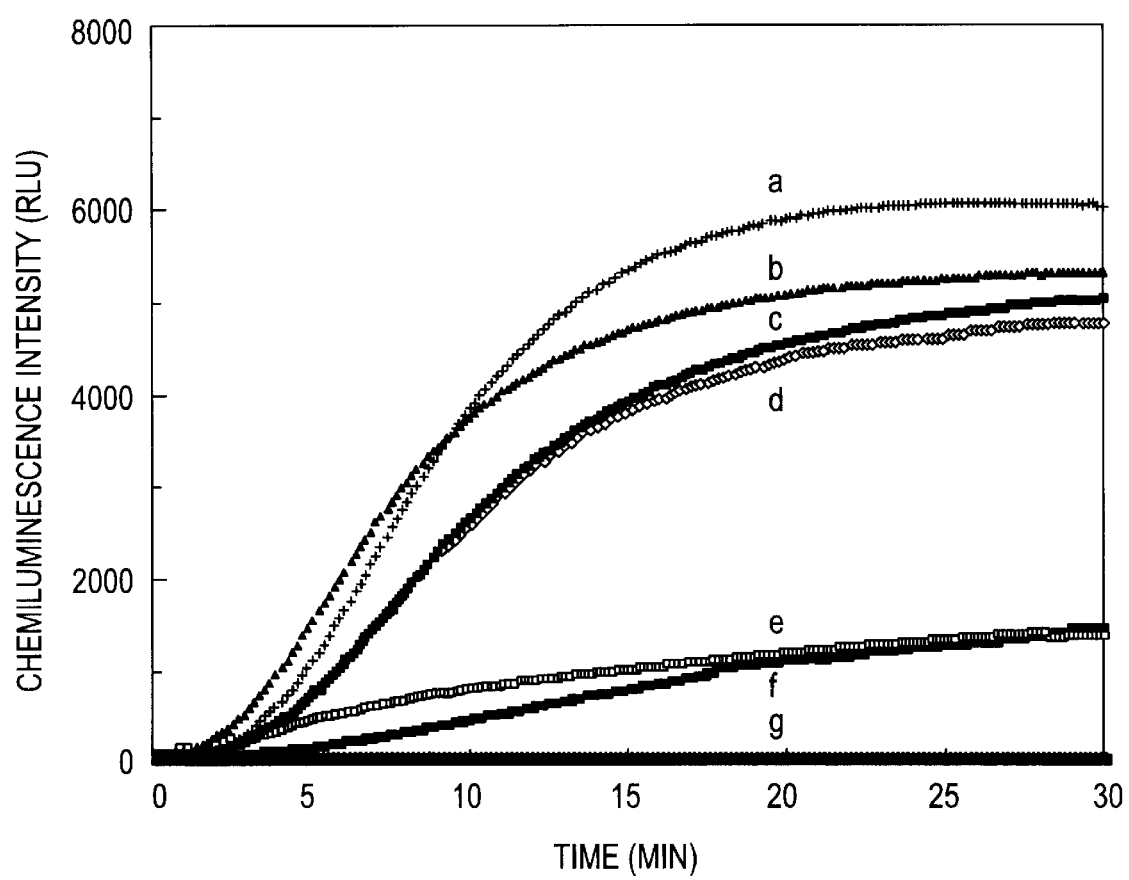
FIG. 4 is a plot showing the time profile of chemiluminescence emission as a function of the concentration of 4-hydroxyphenyl phosphate. A reagent composition consisting of a 0.33 mM solution of acridan phosphate 1 and 0.88 mM $MgCl_2$ in 0.2M 221 buffer, pH 9.6 containing varying concentrations of 4-hydroxyphenyl phosphate (in mg/mL a, 1; b, 3.3; c, 0.66; d, 0.83; e, 10; f, 0.1; g, 0) was reacted with $8 \times 10^{-17}$ mol of AP at 25° C.

A study was performed to determine the range of concentrations of protected dihydroxyaromatic compound useful in chemiluminescent assays of a hydrolytic enzyme. A reagent consisting of a 0.33 mM solution of acridan phosphate 1 and 0.88 mM $MgCl_2$ in 0.2M 221 buffer, pH 9.6 containing concentrations of 4-hydroxyphenyl phosphate varying from 0 to 10 mM was reacted with $8\times10^{-17}$ mol of AP at 25° C. (in mg/mL: a, 1; b, 3.3; c, 0.66; d, 0.83; e, 10; f, 0.1; g, 0). FIG. 4 depicts the various kinetic profiles of chemiluminescence emission. The fact that the solution lacking 4-hydroxyphenyl phosphate produced almost no chemiluminescence demonstrates that light emission is not due simply to removal of the phosphate protecting group from 1 by AP followed by autoxidation of the enolate.

Example 18

Linearity of Detection of AP with Acridan Phosphate 1 in a One Step Assay

Figure 5:
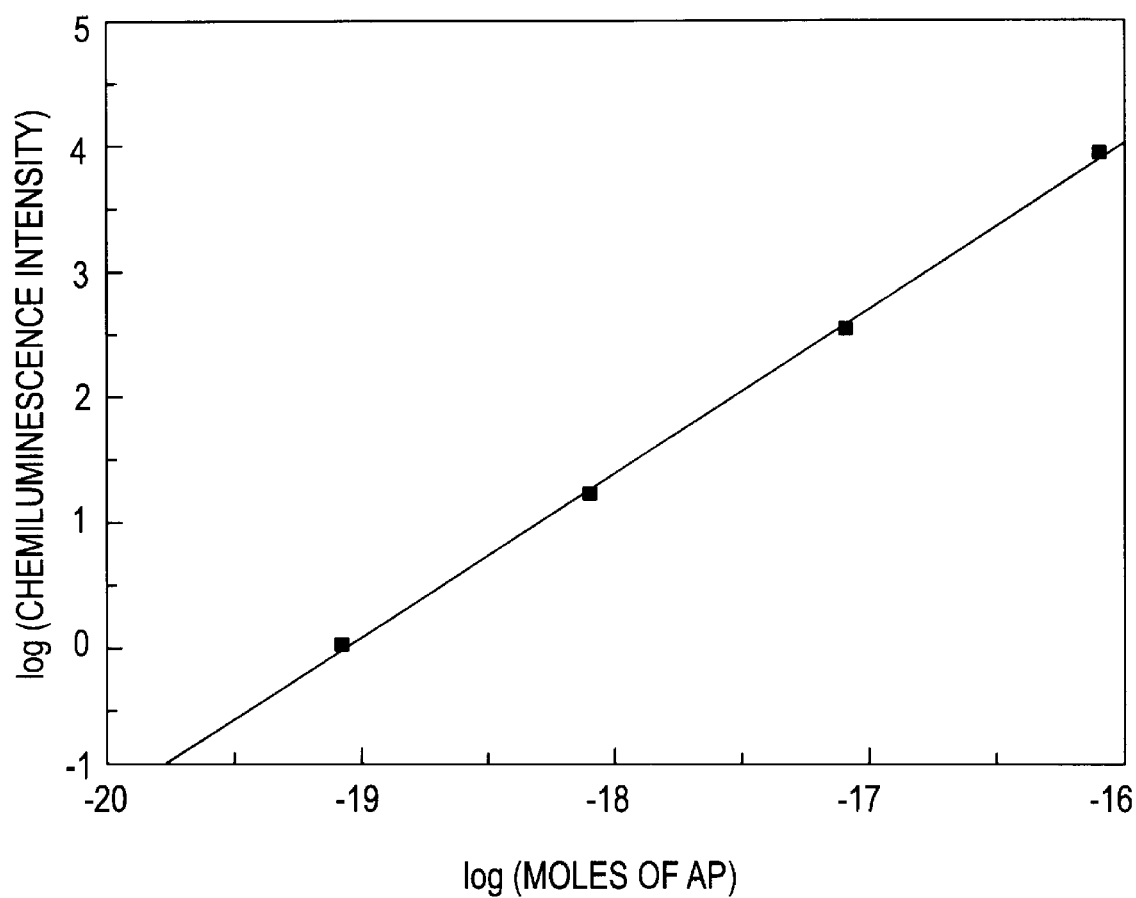
FIG. 5 is a graph relating the amount of AP to chemiluminescence intensity emitted by 100 $\mu L$ of a reagent composition comprising 0.66 mM acridan phosphate 1, 0.66 mM 4-hydroxyphenyl phosphate and 0.88 mM $MgCl_2$ in 0.2M 221 buffer, pH 9.6. The composition (100 $\mu L$) was reacted with 10 $\mu L$ of solutions of AP containing between $8 \times 10^{-15}$ and $8 \times 10^{-20}$ mol of enzyme or 10 $\mu L$ of water as a reagent blank at ambient temperature in the wells of a black microplate. Light intensity was measured after 25 min. Less than 0.1 amol of AP was detected.

A chemiluminescent assay of AP was performed by reacting varying quantities of AP with 100 µL portions of a reagent composition comprising 0.66 mM acridan phosphate 1, 0.66 mM 4-hydroxyphenyl phosphate and 0.88nM $MgCl_2$ in 0.2M 221 buffer, pH 9.6 at 25° C. placed in a 96-well plate housed in a Labsystems Luminoskan luminometer. Light intensity measured at 25 min correlated with amount of enzyme in the range $8\times10^{-17}$–$8\times10^{-20}$ mol as shown in FIG. 5.

Example 19

Chemiluminescent Detection of β-Galactosidase

Figure 6:
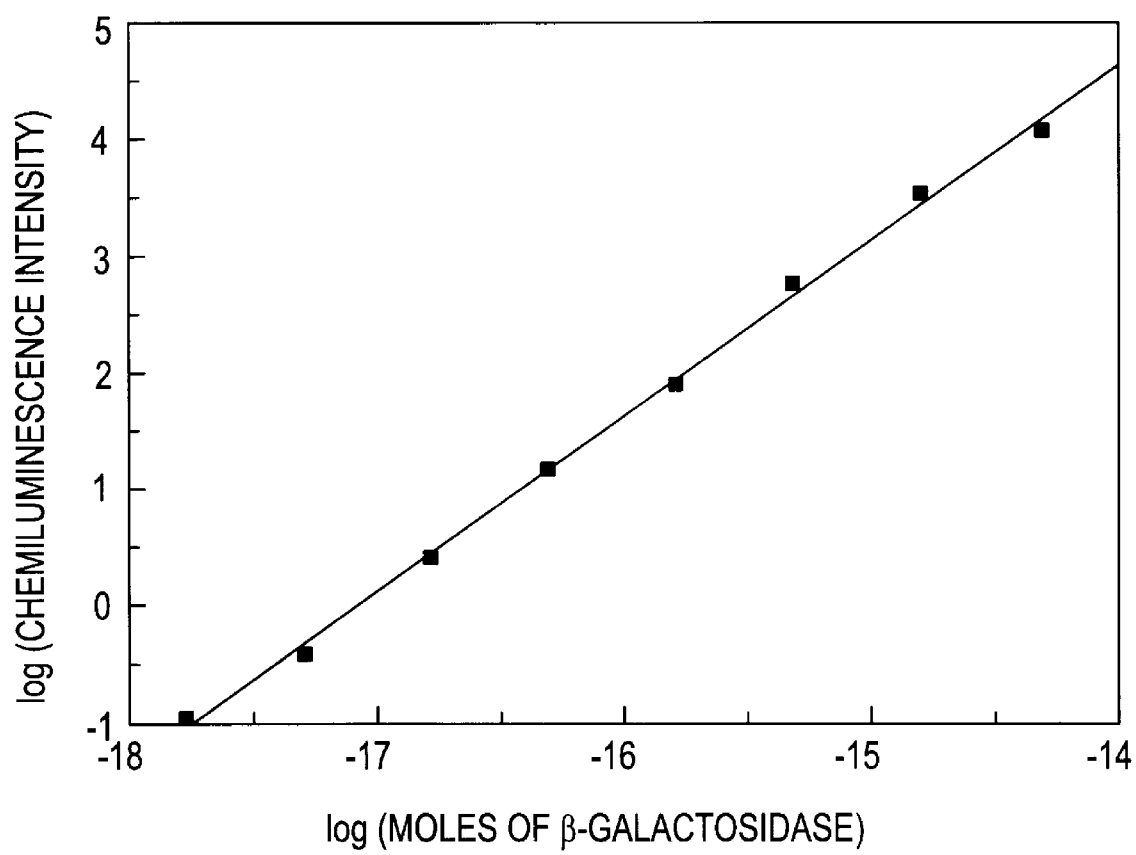
FIG. 6 is a graph relating the amount of β-galactosidase to chemiluminescence intensity. Solutions of 4-hydroxy phenyl β-galactoside (1 mM) in 0.05M phosphate buffer, pH 7.5, 0.01M NaCl, 3 mM $MgCl_2$ were incubated with dilutions of β-galactosidase at 37° C. for 35 min. Portions were reacted with an equal volume of a solution of acridan phosphate 3 having the following composition: 0.2M 221 buffer, pH 9.6, 0.88 mM $MgCl_2$, 0.66 mM acridan phosphate 3, and 0.1% SDS. The amount of enzyme in the wells ranged from $4.9 \times 10^{-15}$ to $1.6 \times 10^{-18}$ mol of β-galactosidase. Chemiluminescence intensity was measured at 5 min

A stock solution of β-galactosidase (Grade VIII, cat. No. G 5635, Sigma Chemical Co.) was serially diluted in 0.01M phosphate buffer, pH 7.0, 0.01M NaCl, 0.01M $MgCl_2$ to contain between $4.9\times10^{-15}$ and $1.6\times10^{-18}$ mol of enzyme/µL. 130 µL Aliquots of a 1 mM solution of 4-hydroxyphenyl-β-D-galactoside in 0.05M phosphate buffer, pH 7.5, 0.01M NaCl, 3 mM $MgCl_2$ were incubated with 2.6 µL of each the enzyme dilutions at 37° C. for 35 min. Duplicate 50 µL portions were transferred into black microwell strips and cooled to room temperature. A 50 µL portion of a solution of acridan phosphate 3 having the following composition: 0.2M 221 buffer, pH 9.6, 0.88 mM $MgCl_2$, 0.66 mM acridan phosphate 3, and 0.1% SDS was injected into each well. The amount of enzyme in the wells ranged from $4.9\times10^{-15}$ and $1.6\times10^{-18}$ mol of β-galactosidase. Chemiluminescence intensity measured at 5 min in relation to the amount of β-galactosidase is shown in FIG. 6.

Example 20

Chemiluminescent Detection of β-Glucuronidase

Figure 7:
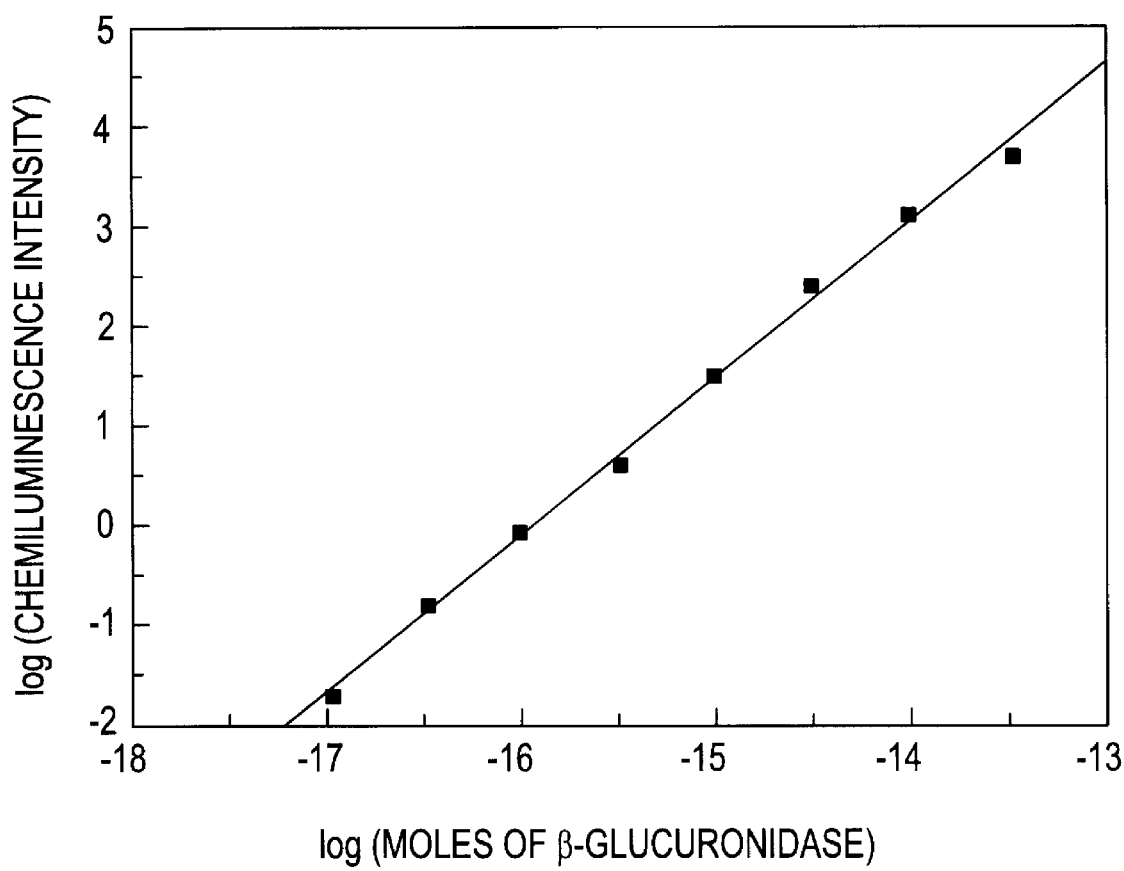
FIG. 7 is a graph relating the amount of β-glucuronidase to chemiluminescence intensity. Solutions of 4-hydroxy phenyl β-glucuronide (1 mM) in 0.05M phosphate buffer, pH 7.0, 0.01M NaCl were incubated with dilutions of β-glucuronidase at 37° C. for 30 min. Portions were reacted with an equal volume of a solution of acridan phosphate 4 having the following composition: 0.2M 221 buffer, pH 9.6, 0.88 mM $MgCl_2$, 0.66 mM acridan phosphate 4, and 0.1% SDS. The amount of enzyme in the wells ranged from $3.3 \times 10^{-14}$ to $3.3 \times 10^{-18}$ mol of β-glucuronidase. Chemiluminescence intensity was measured at 11 min.
Figure 8:
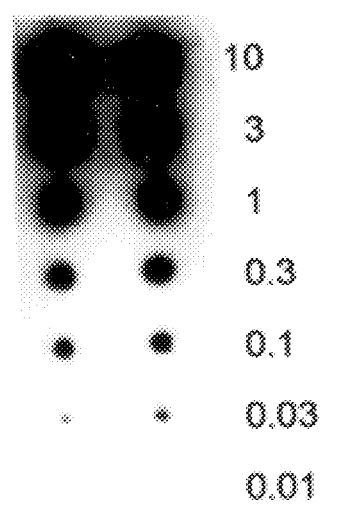
FIG. 8 is an image of a dot blot analysis of dilutions of DNA using a reagent composition containing 0.66 mM acridan phosphate 4, 0.66 mM 4-hydroxyphenyl phosphate, 0.1% SDS and 0.88 mM $MgCl_2$ in 0.1M 221 buffer, pH 9.6. The image is the result of a 1 min exposure taken 3 h after contacting the membrane with detection reagent.

A stock solution of β-glucuronidase (type X-A, cat. No. G 7896, Sigma Chemical Co., MW=290,000) was serially diluted in 0.01M phosphate buffer, pH 7.0, 0.15M NaCl to contain between $3.3\times10^{-14}$ and $3.3\times10^{-18}$ mol of enzyme/ μL. 130 μL Aliquots of a 1 mM solution of 4-hydroxyphenyl-β-D-glucuronide in 0.05M phosphate buffer, pH 7.0, 0.01M NaCl were incubated with 2.6 μL of each the enzyme dilutions at 37° C. for 30 min. Duplicate 50 μL portions were transferred into black microwell strips and cooled to room temperature. A 50 μL portion of a solution of acridan phosphate 4 having the following composition: 0.2M 221 buffer, pH 9.6, 0.88 mM $MgCl_2$, 0.66 mM acridan phosphate 4, and 0.1% SDS was injected into each well. Chemiluminescence intensity measured at 11 min in relation to the amount of β-glucuronidase is shown in FIG. 7.

Example 21

Western Blot Assay using an Alkaline Phosphatase-Conjugate

Compositions of the present invention were used to detect and quantify a protein antigen, β-galactosidase in a Western blot with an AP-labeled antibody on a nitrocellulose membrane. Dilutions of β-galactosidase containing from 5000, 1000, 180, 30 and 5 pg, respectively, of protein were electrophoresed and transferred to nitrocellulose membranes (Hybond ECL, Amersham, Arlington Heights, Ill.). The membranes were blocked with 1% non-fat milk (NFM) in T-TBS (0.05% Tween 20 in TBS; TBS is 50 mmol/L Tris-HCl, pH 7.4, 0.15 mol/L NaCl) for 1 h at room temperature and then treated sequentially with a 1:1500 dilution of a 3.3 μg/mL solution of mouse anti-β-galactosidase in blocking buffer, T-TBS wash buffer and then a 1:600 dilution of a 416 mU/mL solution of sheep anti-mouse IgG-AP conjugate. After washing with T-TBS, the membranes were soaked briefly with a detection reagent comprising 0.2M 221 buffer, pH 9.6 containing 0.88 mM $MgCl_2$, 0.66 mM hydroquinone phosphate disodium salt, 0.66 mM acridan phosphate 3 and 0.1% SDS. The membranes were placed between transparent plastic sheets and exposed to X-ray film. All five bands of β-galactosidase were detected after 15 min with a 1 min exposure. The light produced using these compositions led to intense emission which could be imaged for at least 1 day.

Example 22

Dot Blot Assay

A representative example of the use of a reagent of the present invention in a dot blot assay is demonstrated in the following example.

Digoxigenin-labeled DNA (pBR328), anti-digoxigenin-AP conjugate were supplied as a kit (Genius 3, Boehringer-Mannheim, Indianapolis, Ind.), blocking buffer and positively charged nylon membrane were obtained from Boehringer-Mannheim. The wash buffer was 0.1M maleic acid, pH 7.5, 0.15M NaCl, 0.05% SDS. The detection reagent comprised 0.66 mM acridan phosphate 2, 0.66 mM 4-hydroxyphenyl phosphate, 0.88 mM $MgCl_2$, 0.1% SDS in 0.2M 221 buffer, pH 9.6.

DNA dilutions (10, 3, 1, 0.3, 0.1, 0.03, 0.01 pg) were dot blotted onto nylon membranes, blocked, washed and reacted with antibody-AP conjugate according to manufacturer's protocol. Excess buffer was drained off and blots soaked in a detection reagent described in for 3 min. Excess reagent was drained off, and the blots placed between transparent sheets and exposed to X-ray film for varying lengths of time. An immediate 1 min exposure detected the 10 pg–0.3 pg spots. After 30 min, all seven spots were detected with a 20 min exposure. Multiple exposures could be performed for several days. For example, after 5 days, all seven spots were detected with a 1–5 min exposure. Detection reagents containing 0.66 mM acridan phosphate 3, or 0.66 mM solution of a mixture of 2- and 3-chloro-4-hydroxyphenyl phosphate produced comparable results.

The foregoing description and examples are illustrative only and not to be considered as restrictive. It is to be recognized that modifications of the specific compounds and methods not specifically disclosed can be made without departing from the spirit and scope of the present invention which is limited only by the appended claims.

What is claimed is:

1. A method of generating chemiluminescence comprising reacting in the presence of oxygen a) a dihydroxyaromatic compound which comprises from 1–5 carbocyclic aromatic rings and which is substituted with two hydroxy groups separated by an even number of ring carbon atoms; and b) a heterocyclic enol phosphate compound having the formula

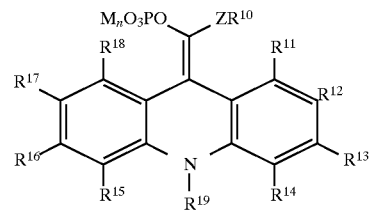

wherein $R^{10}$ is an organic group containing up to 50 non-hydrogen atoms selected from C, N, O, S, P and halogen atoms, each of $R^{11}$–$R^{18}$ is independently selected from hydrogen, alkyl, substituted alkyl, aryl, substituted aryl, aralkyl, substituted aralkyl, alkenyl, alkynyl, alkoxy, aryloxy, halogen, amino, substituted amino, carboxyl, carboalkoxy, carboxamide, cyano, and sulfonate groups, and wherein pairs of adjacent groups can complete a benzo-fused ring, $R^{19}$ is an organic group containing up to 50 non-hydrogen atoms selected from C, N, O, S, P and halogen atoms, Z is selected from O and S atoms, each M is independently selected from H and a cationic center and n is a number which satisfies electroneutrality; and provided that any one of $R^{11}$–$R^{18}$ or a substituent on any one of $R^{10}$–$R^{19}$ can be a group —A—Q wherein A is a spacer group selected from $C_1$–$C_{10}$ alkylene and $C_2$–$C_{10}$ oxyalkylene groups and Q is a linking group capable of forming a covalent bond selected from halogen, diazo, —NCO, —NCS, —CHO, acid anhydride, oxiranyl, succinimidoxycarbonyl, maleimide, cyano, triazole, tetrazole, hydroxyl, —COOH, thiol, primary amino and secondary amino groups.

2. The method of claim 1 wherein the dihydroxyaromatic compound comprises an aromatic ring system selected from benzene, biphenyl, naphthalene, and anthracene rings.

3. The method of claim 1 wherein the dihydroxyaromatic compound has the formula I

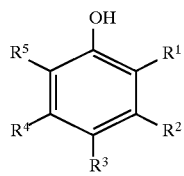

wherein at least one of $R^1$ and $R^3$ is an OH group, the other one of $R^1$ or $R^3$ and $R^2$, $R^4$ and $R^5$ are each independently selected from hydrogen, alkyl, alkoxy, alkenyl, alkynyl, aryl, aralkyl, amino, aminoalkyl, carboxyl —C(=O)OH, carboxyl ester —C(=O)OR$^6$, formyl —C(=O)H, alkylcarboxy —OC(=O)R$^6$, arylcarboxy —OC(=O)R$^9$ and halogen groups, pairs of adjacent groups, when taken together, can complete a five or six-membered aliphatic or aromatic ring, $R^6$ is a lower alkyl group, $R^7$ and $R^8$ are each H or a lower alkyl group and $R^9$ is an aryl ring group.

4. The method of claim 3 wherein the group $R^3$ in the compound of formula I is the OH group and $R^1$, $R^2$, $R^4$ and $R^5$ are independently selected from hydrogen, alkyl, alkoxy, halogen, aryl and aralkyl groups.

5. The method of claim 3 wherein the group $R^3$ in the compound of formula I is the OH group, $R^2$, $R^4$ and $R^5$ are each hydrogen and wherein $R^1$ is selected from hydrogen, alkyl, alkoxy, halogen, aryl and aralkyl groups.

6. The method of claim 1 wherein the group $R^{19}$ in the heterocyclic enol phosphate compound is selected from substituted and unsubstituted lower alkyl groups and substituted and unsubstituted benzyl groups.

7. The method of claim 1 wherein the group $R^{10}$ in the heterocyclic enol phosphate compound is selected from alkyl, substituted alkyl, aryl, substituted aryl, aralkyl and substituted aralkyl groups.

8. The method of claim 1 wherein the heterocyclic enol phosphate compound has the formula

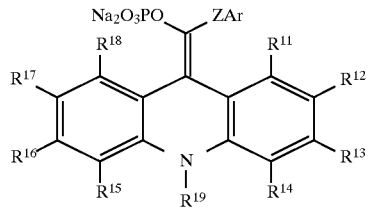

wherein Z is O or S, Ar is selected from a phenyl group, a substituted phenyl group and a naphthyl group, $R^{19}$ is a lower alkyl group and each of $R^{11}$ to $R^{18}$ is independently selected from hydrogen and lower alkoxy groups.

9. The method of claim 5 wherein the heterocyclic enol phosphate compound has the formula

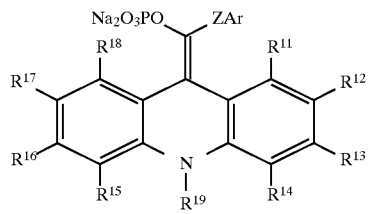

wherein Z is O or S, Ar is selected from a phenyl group, a substituted phenyl group and a naphthyl group, $R^{19}$ is a lower alkyl group and each of $R^{11}$ to $R^{18}$ is independently selected from hydrogen and lower alkoxy groups.

10. The method of claim 1 wherein the heterocyclic enol phosphate compound is selected from

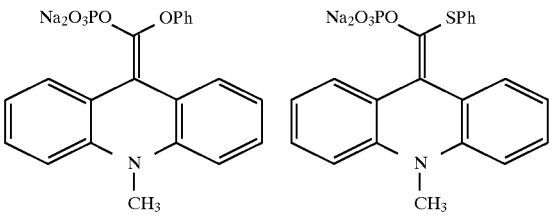

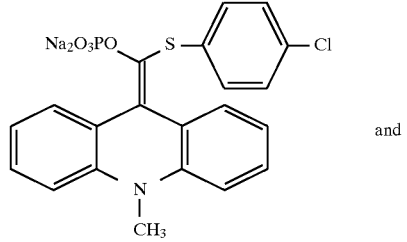

and

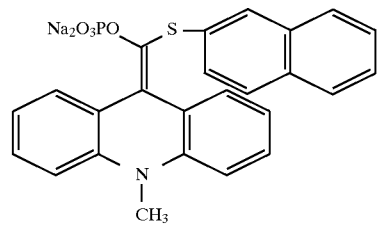

11. The method of claim 5 wherein the heterocyclic enol phosphate compound is selected from

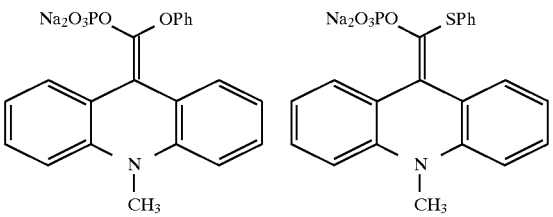

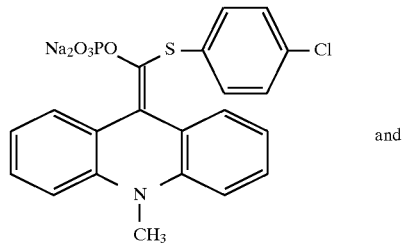

and

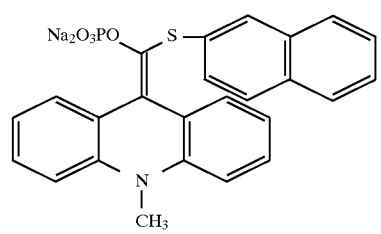

12. The method of claim 1 wherein the heterocyclic enol phosphate compound contains the group —A—Q.

13. The method of claim 8 wherein the heterocyclic enol phosphate compound contains the group —A—Q as a substituent on $R^{10}$ or $R^{19}$ or at any one of the $R^{11}$–$R^{18}$ positions.

14. The method of claim 1 wherein oxygen is supplied dissolved in a solution containing the dihydroxyaromatic compound and heterocyclic enol phosphate compound at equilibrium with the atmosphere.

15. The method of claim 1 wherein the dihydroxyaromatic compound and heterocyclic enol phosphate compound are present in a solution comprising an aqueous buffer having a pH between about 7 and about 10.5, the dihydroxyaromatic compound is present at a concentration of 0.001–20mM and the heterocyclic enol phosphate compound at a concentration of 0.001–20 mM.

16. A composition for generating chemiluminescence in the presence of oxygen comprising
    a) a dihydroxyaromatic compound which comprises from 1-5 carbocyclic aromatic rings and which is substituted with two hydroxy groups separated by an even number of ring carbon atoms; and
    b) a heterocyclic enol phosphate compound having the formula

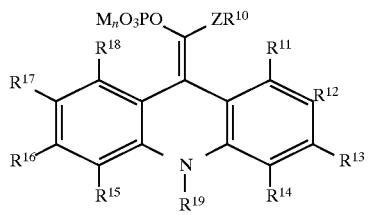

wherein $R^{10}$ is an organic group containing up to 50 non-hydrogen atoms selected from C, N, O, S, P and halogen atoms, each of $R-R^{18}$ is independently selected from hydrogen, alkyl, substituted alkyl, aryl, substituted aryl, aralkyl, substituted aralkyl, alkenyl, alkynyl, alkoxy, aryloxy, halogen, amino, substituted amino, carboxyl, carboalkoxy, carboxamide, cyano, and sulfonate groups, and wherein pairs of adjacent groups can complete a benzo-fused ring, $R^{19}$ is an organic group containing up to 50 non-hydrogen atoms selected from C, N, O, S, P and halogen atoms, Z is selected from O and S atoms, each M is independently selected from H and a cationic center and n is a number which satisfies electroneutrality; and provided that any one of $R^{11}$–$R^{18}$ or a substituent on any one of $R^{10}$–$R^{19}$ can be a group —A—Q wherein A is a spacer group selected from $C_1$–$C_{10}$ alkylene and $C_2$–$C_{10}$oxyalkylene groups and Q is a linking group capable of forming a covalent bond selected from halogen, diazo, —NCO, —NCS, —CHO, acid anhydride, oxiranyl, succinimidoxycarbonyl, maleimide, cyano, triazole, tetrazole, hydroxyl, —COOH, thiol, primary amino and secondary amino groups.

17. The composition of claim 16 wherein the dihydroxyaromatic compound comprises an aromatic ring system selected from benzene, biphenyl, naphthalene, and anthracene rings.

18. The composition of claim 16 wherein the dihydroxyaromatic compound has the formula I

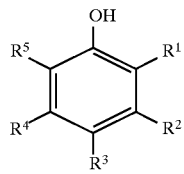

wherein at least one of $R^1$ and $R^3$ is an OH group, the other one of $R^1$ or $R^3$ and $R^2$, $R^4$ and $R^5$ are each independently selected from hydrogen, alkyl, alkoxy, alkenyl, alkynyl, aryl, aralkyl, amino, aminoalkyl, carboxyl —C(=O)OH, carboxyl ester —C(=O)OR⁶, formyl —C(=O)H, alkylcarboxy —OC(=O)R⁶, arylcarboxy —OC(=O)R⁹ and halogen groups, pairs of adjacent groups, when taken together, can complete a five or six-membered aliphatic or aromatic ring, $R^6$ is a lower alkyl group, $R^7$ and $R^8$ are each H or a lower alkyl group and $R^9$ is an aryl ring group.

19. The composition of claim 18 wherein the group $R^3$ in the compound of formula I is the OH group and $R^1$, $R^2$, $R^4$ and $R^5$ are independently selected from hydrogen, alkyl, alkoxy, halogen, aryl and aralkyl groups.

20. The composition of claim 18 wherein the group $R^3$ in the compound of formula I is the OH group, $R^2$, $R^4$ and $R^5$ are each hydrogen and $R^1$ is selected from hydrogen, alkyl, alkoxy, halogen, aryl and aralkyl groups.

21. The composition of claim 16 wherein the group $R^{19}$ in the heterocyclic enol phosphate compound is selected from substituted and unsubstituted lower alkyl groups and substituted and unsubstituted benzyl groups.

22. The composition of claim 16 wherein the group $R^{10}$ in the heterocyclic enol phosphate compound is selected from alkyl, substituted alkyl, aryl, substituted aryl, aralkyl and substituted aralkyl groups.

23. The composition of claim 16 wherein the heterocyclic enol phosphate compound has the formula

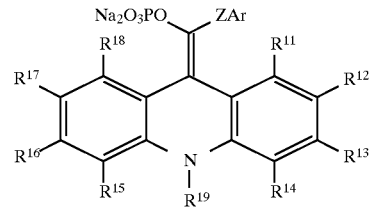

wherein Z is O or S, wherein Ar is selected from a phenyl group, a substituted phenyl group and a naphthyl group, wherein $R^{19}$ is a lower alkyl group and wherein each of $R^{11}$ to $R^{18}$ is independently selected from hydrogen and lower alkoxy groups.

24. The composition of claim 20 wherein the heterocyclic enol phosphate compound has the formula

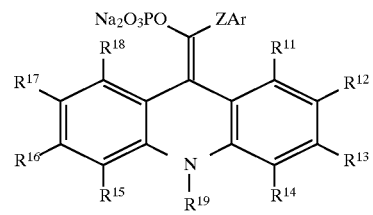

wherein Z is O or S, wherein Ar is selected from a phenyl group, a substituted phenyl group and a naphthyl group, wherein $R^{19}$ is a lower alkyl group and wherein each of $R^{11}$ to $R^{18}$ is independently selected from hydrogen and lower alkoxy groups.

25. The composition of claim 16 wherein the heterocyclic enol phosphate compound is selected from

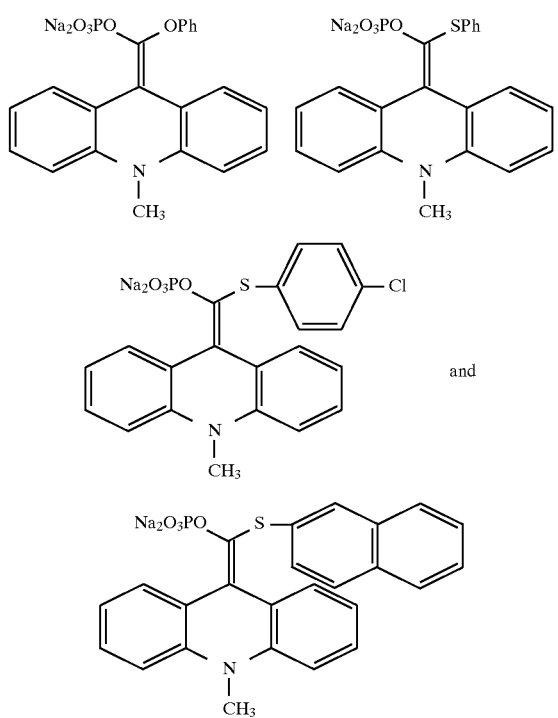

26. The composition of claim 20 wherein the heterocyclic enol phosphate compound is selected from

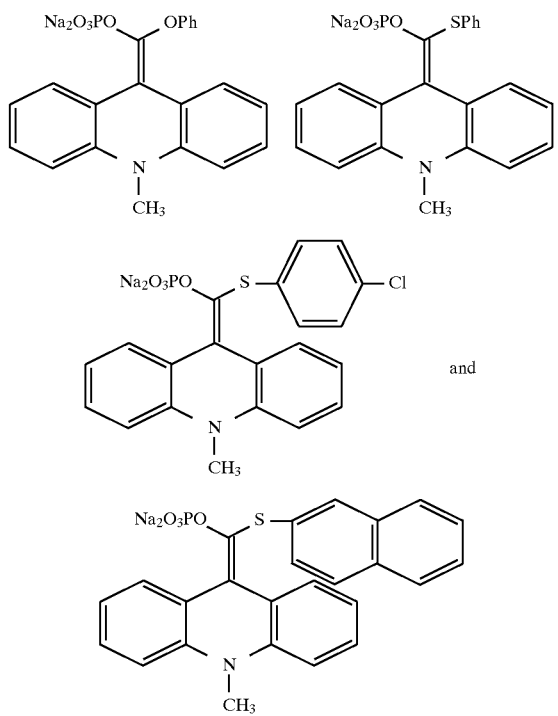

27. The composition of claim 16 wherein the heterocyclic enol phosphate compound contains the group —A—Q.

28. The composition of claim 27 wherein the heterocyclic enol phosphate compound contains the group —A—Q as a substituent on $R^{10}$ or $R^{19}$ or at any one of the $R^{11}$–$R^{18}$ positions.

29. The composition of claim 16 comprising an aqueous buffer having a pH in the range 7–10.5, containing the dihydroxyaromatic compound at a concentration of 0.001–20 mM and the heterocyclic enol phosphate compound at a concentration of 0.001–20 mM.

30. The composition of claim 29 having a pH in the range of 8–10 and containing the dihydroxyaromatic compound at a concentration of about 0.05–5 mM and the heterocyclic enol phosphate compound at a concentration of about 0.05–5 mM.

31. The method of claim 1 further comprising producing the dihydroxyaromatic compound by reacting a protected dihydroxyaromatic compound in which one hydroxy group of a dihydroxyaromatic compound is protected by an enzyme-cleavable group X with a hydrolytic enzyme to remove the enzyme-cleavable group.

32. The method of claim 31 wherein the reaction of the hydrolytic enzyme with the protected dihydroxyaromatic compound is performed in the absence of the heterocyclic enol phosphate.

33. The method of claim 31 wherein the reaction of the hydrolytic enzyme with the protected dihydroxyaromatic compound is performed in the presence of the heterocyclic enol phosphate.

34. The method of claim 31 wherein the hydrolytic enzyme is selected from alkaline phosphatase, acid phosphatase, β-galactosidase, β-glucuronidase and β-glucosidase and the enzyme-cleavable group is selected from phosphate, β-galactoside, β-glucuronide and β-glucoside groups.

35. The method of claim 31 wherein the protected dihydroxyaromatic compound has the formula

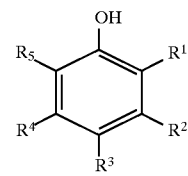

wherein one of $R^1$ or $R^3$ is an OX group, wherein X is the enzyme-cleavable group, the other one of $R^1$ or $R^3$ and $R^2$, $R^4$ and $R^5$ are each independently selected from hydrogen, alkyl, alkoxy, alkenyl, alkynyl, aryl, aralkyl, amino, aminoalkyl, carboxyl —C(=O)OH, carboxyl ester —C(=O)OR$^6$, formyl —C(=O)H, alkylcarboxy —OC(=O)R$^6$, arylcarboxy —OC(=O)R$^9$ and halogen groups, pairs of adjacent groups, when taken together, can complete a benzo-fused ring, $R^6$ is a lower alkyl group, $R^7$ and $R^8$ are each H or a lower alkyl group and $R^9$ is an aryl ring group.

36. The method of claim 35 wherein $R^3$ is the OX group, $R^2$, $R^4$ and $R^5$ are each hydrogen and $R^1$ is selected from hydrogen, alkyl, alkoxy, halogen, aryl and aralkyl groups.

37. The method of claim 31 wherein the heterocyclic enol phosphate compound has the formula

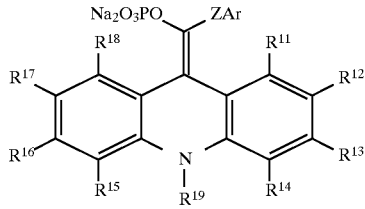

wherein Z is O or S, Ar is selected from a phenyl group, a substituted phenyl group and a naphthyl group, $R^{19}$ is a lower alkyl group and each of $R^{11}$ to $R^{18}$ is independently selected from hydrogen and lower alkoxy groups.

38. The method of claim 31 wherein the heterocyclic enol phosphate compound is selected from

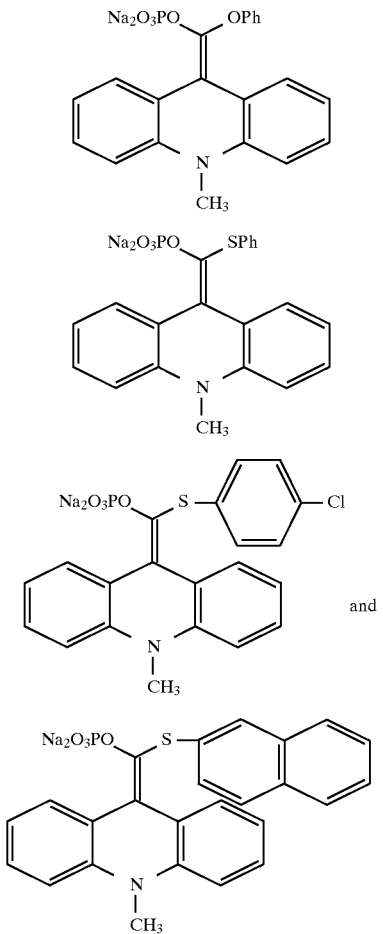

39. A composition for generating chemiluminescence by reaction with a hydrolytic enzyme comprising:
   a) a protected dihydroxyaromatic compound which comprises from 1–5 carbocyclic aromatic rings and which is substituted with two hydroxy groups separated by an even number of ring carbon atoms, wherein one hydroxy group is protected by an enzyme-cleavable group X; and
   b) a heterocyclic enol phosphate compound having the formula

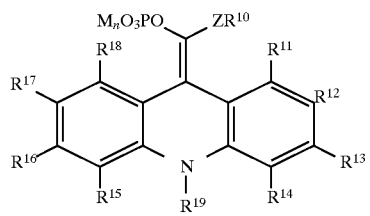

wherein $R^{10}$ is an organic group containing up to 50 non-hydrogen atoms selected from C, N, O, S, P and halogen atoms, each of $R^{11}$–$R^{18}$ is independently selected from hydrogen, alkyl, substituted alkyl, aryl, substituted aryl, aralkyl, substituted aralkyl, alkenyl, alkynyl, alkoxy, aryloxy, halogen, amino, substituted amino, carboxyl, carboalkoxy, carboxamide, cyano, and sulfonate groups, and wherein pairs of adjacent groups can complete a benzo-fused ring, $R^{19}$ is an organic group containing up to 50 non-hydrogen atoms selected from C, N, O, S, P and halogen atoms, Z is selected from O and S atoms, each M is independently selected from H and a cationic center and n is a number which satisfies electroneutrality.

40. The composition of claim 39 wherein the dihydroxyaromatic compound comprises an aromatic ring system selected from benzene, biphenyl, naphthalene, and anthracene rings.

41. The composition of claim 39 wherein the protected dihydroxyaromatic compound has the formula I

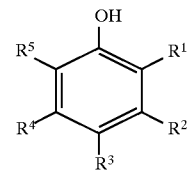

wherein at least one of $R^1$ and $R^3$ is an OX group, the other one of $R^1$ or $R^3$ and $R^2$, $R^4$ and $R^5$ are each independently selected from hydrogen, alkyl, alkoxy, alkenyl, alkynyl, aryl, aralkyl, amino, aminoalkyl, carboxyl —C(=O)OH, carboxyl ester —C(=O)OR$^6$, formyl —C(=O)H, alkylcarboxy —OC(=O)R$^6$, arylcarboxy —OC(=O)R$^9$ and halogen groups wherein pairs of adjacent groups, when taken together, can complete a five or six-membered aliphatic or aromatic ring, $R^6$ is a lower alkyl group, $R^7$ and $R^8$ are each H or a lower alkyl group and $R^9$ is an aryl ring group.

42. The composition of claim 41 wherein the group $R^3$ in the compound of formula I is the OX group and $R^1$, $R^2$, $R^4$ and $R^5$ are independently selected from hydrogen, alkyl, alkoxy, halogen, aryl and aralkyl groups.

43. The composition of claim 41 wherein the group $R^3$ in the compound of formula I is the OX group, $R^2$, $R^4$ and $R^5$ are each hydrogen and $R^1$ is selected from hydrogen, alkyl, alkoxy, halogen, aryl and aralkyl groups.

44. The composition of claim 39 wherein the group $R^{19}$ in the heterocyclic enol phosphate compound is selected from substituted and unsubstituted lower alkyl groups and substituted and unsubstituted benzyl groups.

45. The composition of claim 39 wherein the group $R^{10}$ in the heterocyclic enol phosphate compound is selected from alkyl, substituted alkyl, aryl, substituted aryl, aralkyl and substituted aralkyl groups.

46. The composition of claim 39 wherein the heterocyclic enol phosphate compound has the formula

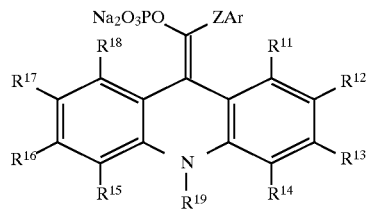

wherein Z is O or S, Ar is selected from a phenyl group, a substituted phenyl group and a naphthyl group, $R^{19}$ is a lower alkyl group and each of $R^{11}$ to $R^{18}$ is independently selected from hydrogen and lower alkoxy groups.

47. The composition of claim 41 wherein the heterocyclic enol phosphate compound has the formula

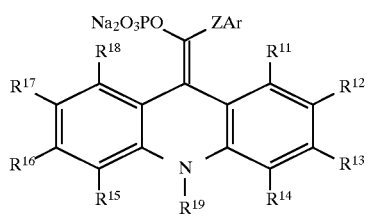

wherein Z is O or S, Ar is selected from a phenyl group, a substituted phenyl group and a naphthyl group, $R^{19}$ is a lower alkyl group and each of $R^{11}$ to $R^{18}$ is independently selected from hydrogen and lower alkoxy groups.

48. The composition of claim 39 wherein the heterocyclic enol phosphate compound is selected from

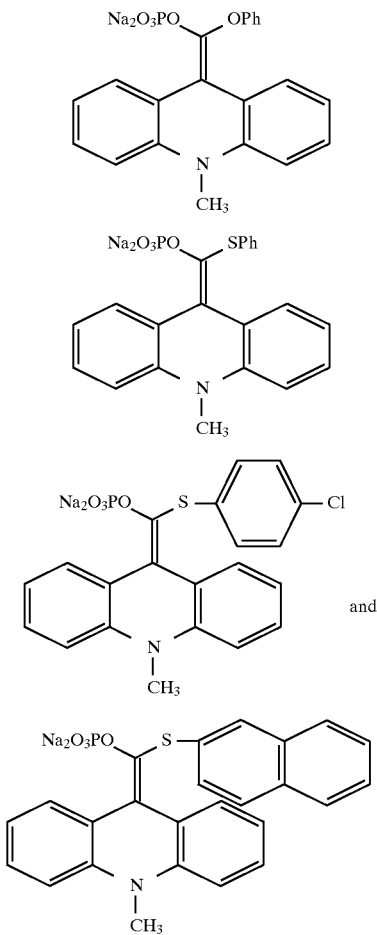

and

49. The composition of claim 39 comprising an aqueous buffer having a pH in the range 7–10.5, containing the protected dihydroxyaromatic compound at a concentration of 0.001–20 mM and the heterocyclic enol phosphate compound at a concentration of 0.001–20 mM.

50. The composition of claim 49 having a pH in the range of 8–10 and containing the protected dihydroxyaromatic compound at a concentration of about 0.05–5 mM and the heterocyclic enol phosphate compound at a concentration of about 0.05–5 mM.

51. The composition of claim 49 additionally comprising an anionic surfactant.

52. The composition of claim 51 wherein the anionic surfactant is a $C_{10}$–$C_{20}$ alkyl sulfate.

53. The composition of claim 51 wherein the anionic surfactant is sodium dodecyl sulfate.

54. A method of conducting an assay of an analyte comprising:
a) reacting in the presence of oxygen a dihydroxyaromatic compound which comprises from 1–5 carbocyclic aromatic rings and which is substituted with two hydroxy groups separated by an even number of ring carbon atoms with a heterocyclic enol phosphate compound to produce chemiluminescence wherein the heterocyclic enol phosphate compound has the formula

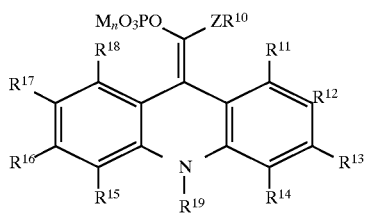

wherein $R^{10}$ is an organic group containing up to 50 non-hydrogen atoms selected from C, N, O, S, P and halogen atoms, each of $R^{11}$–$R^{18}$ is independently selected from hydrogen, alkyl, substituted alkyl, aryl, substituted aryl, aralkyl, substituted aralkyl, alkenyl, alkynyl, alkoxy, aryloxy, halogen, amino, substituted amino, carboxyl, carboalkoxy, carboxamide, cyano, and sulfonate groups, and wherein pairs of adjacent groups can complete a benzo-fused ring, $R^{19}$ is, an organic group containing up to 50 non-hydrogen atoms selected from C, N, O, S, P and halogen atoms, Z is selected from O and S atoms, each M is independently selected from H and a cationic center and n is a number which satisfies electroneutrality; and provided that any one of $R^{11}$–$R^{18}$ or a substituent on any one of $R^{10}$–$R^{19}$ can be a group —A—Q wherein A is a spacer group selected from $C_1$–$C_{10}$ alkylene and $C_2$–$C_{10}$ oxyalkylene groups and Q is a linking group capable of forming a covalent bond selected from halogen, diazo, —NCO, —NCS, —CHO, acid anhydride, oxiranyl, succinimidoxycarbonyl, maleimide, cyano, triazole, tetrazole, hydroxyl, —COOH, thiol, primary amino and secondary amino groups;
b) measuring the chemiluminescence; and
c) relating the chemiluminescence to the amount of the analyte.

55. The method of claim 54 wherein the dihydroxyaromatic compound comprises an aromatic ring system selected from benzene, biphenyl, naphthalene, and anthracene rings.

56. The method of claim 54 wherein the dihydroxyaromatic compound has the formula I

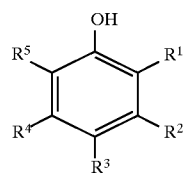

wherein at least one of $R^1$ and $R^3$ is an OH group, the other one of $R^1$ or $R^3$ and $R^2$, $R^4$ and $R^5$ are each independently selected from hydrogen, alkyl, alkoxy, alkenyl, alkynyl, aryl, aralkyl, amino, aminoalkyl, carboxyl —C(=O)OH, carboxyl ester —C(=O)$OR^6$, formyl —C(=O)H, alkylcarboxy —OC(=O)$R^6$, arylcarboxy —OC(=O)$R^9$ and halogen groups, pairs of adjacent groups, when taken together, can complete a five or six-membered aliphatic or aromatic ring, $R^6$ is a lower alkyl group, $R^7$ and $R^8$ are each H or a lower alkyl group and $R^9$ is an aryl ring group.

57. The method of claim 56 wherein the group $R^3$ in the compound of formula I is the OH group and $R^1$, $R^2$, $R^4$ and $R^5$ are independently selected from hydrogen, alkyl, alkoxy, halogen, aryl and aralkyl groups.

58. The method of claim 56 wherein the group $R^3$ in the compound of formula I is the OH group, $R^2$, $R^4$ and $R^5$ are hydrogen and $R^1$ is selected from hydrogen, alkyl, alkoxy, halogen, aryl and aralkyl groups.

59. The method of claim 54 wherein the group $R^{19}$ in the heterocyclic enol phosphate compound is selected from substituted and unsubstituted lower alkyl groups and substituted and unsubstituted benzyl groups.

60. The method of claim 54 wherein the group $R^{10}$ in the heterocyclic enol phosphate compound is selected from alkyl, substituted alkyl, aryl, substituted aryl, aralkyl and substituted aralkyl groups.

61. The method of claim 54 wherein the heterocyclic enol phosphate compound has the formula

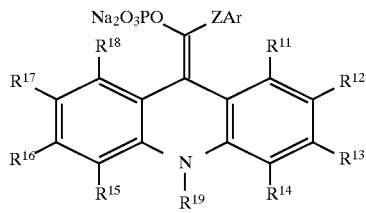

wherein Z is O or S, Ar is selected from a phenyl group, a substituted phenyl group and a naphthyl group, $R^{19}$ is a lower alkyl group and each of $R^{11}$ to $R^{18}$ is independently selected from hydrogen and lower alkoxy groups.

62. The method of claim 56 wherein the heterocyclic enol phosphate compound has the formula

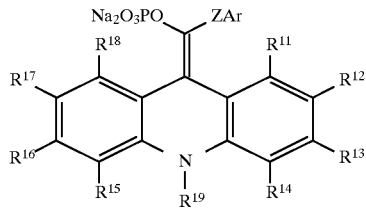

wherein Z is O or S, Ar is selected from a phenyl group, a substituted phenyl group and a naphthyl group, $R^{19}$ is a lower alkyl group and each of $R^{11}$ to $R^{18}$ is independently selected from hydrogen and lower alkoxy groups.

63. The method of claim 54 wherein the heterocyclic enol phosphate compound is selected from

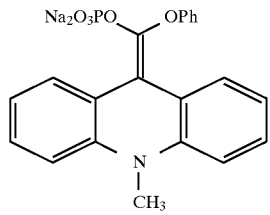

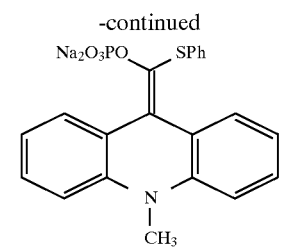

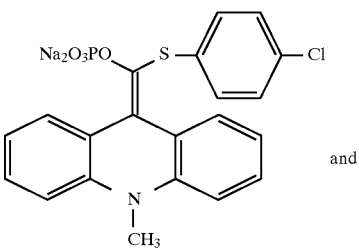

and

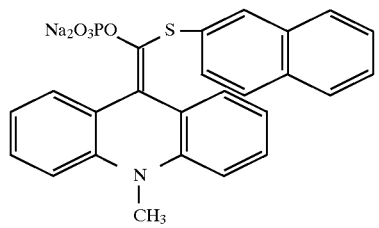

64. The method of claim 56 wherein the heterocyclic enol phosphate compound is selected from

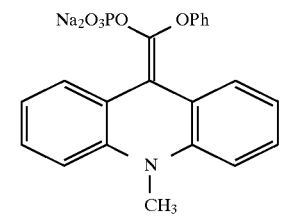

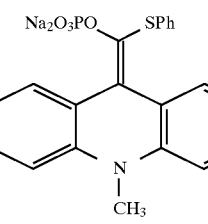

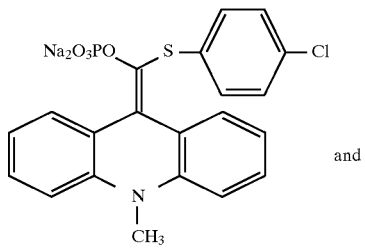

and

-continued

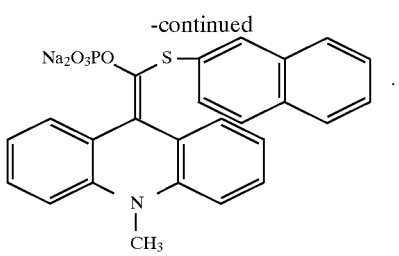

65. The method of claim 54 wherein the heterocyclic enol phosphate compound contains the group —A—Q and further comprising;
  reacting the heterocyclic enol phosphate compound with a specific binding pair member to form a detectably labeled specific binding pair member;
  contacting the labeled specific binding pair member with its specific binding partner to form a labeled specific binding pair; and
  contacting the labeled specific binding pair with the dihydroxyaromatic compound to produce chemiluminescence for detecting the analyte.

66. The method of claim 65 wherein the heterocyclic enol phosphate compound contains the group —A—Q as a substituent on $R^{10}$ or $R^{19}$ or at any one of the $R^{11}$–$R^{18}$ positions.

67. The method of claim 54 further comprising the step of reacting a protected dihydroxyaromatic compound in which one hydroxy group of a dihydroxyaromatic compound is protected with an enzyme-cleavable group X with a hydrolytic enzyme to produce the dihydroxyaromatic compound.

68. The method of claim 67 wherein the reaction of the hydrolytic enzyme with the protected dihydroxyaromatic compound is performed in the absence of the heterocyclic enol phosphate.

69. The method of claim 67 wherein the reaction of the hydrolytic enzyme with the protected dihydroxyaromatic compound is performed in the presence of the heterocyclic enol phosphate.

70. The method of claim 67 wherein the hydrolytic enzyme is s elected from alkaline phosphatase, acid phosphatase, β-galactosidase, β-glucuronidase and β-glucosidase and the enzyme-cleavable group is selected from phosphate, β-galactoside, β-glucuronide and β-glucoside groups.

71. The method of claim 67 wherein the analyte is the hydrolytic enzyme.

72. The method of claim 67 wherein the hydrolytic enzyme is provided as a label on a specific binding pair member.

* * * * *